(12) United States Patent
Wong et al.

(10) Patent No.: US 12,299,875 B2
(45) Date of Patent: May 13, 2025

(54) SLIDE-FREE HISTOLOGICAL IMAGING METHOD AND SYSTEM

(71) Applicant: The Hong Kong University of Science and Technology, Hong Kong (CN)

(72) Inventors: Tsz Wai Wong, Hong Kong (CN); Yan Zhang, Hong Kong (CN); Lei Kang, Hong Kong (CN); Xiufeng Li, Hong Kong (CN); Hei Man Wong, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 338 days.

(21) Appl. No.: 17/597,784

(22) PCT Filed: Aug. 11, 2020

(86) PCT No.: PCT/CN2020/108454
§ 371 (c)(1),
(2) Date: Jan. 24, 2022

(87) PCT Pub. No.: WO2021/052063
PCT Pub. Date: Mar. 25, 2021

(65) Prior Publication Data
US 2022/0237783 A1 Jul. 28, 2022

Related U.S. Application Data

(60) Provisional application No. 62/973,101, filed on Sep. 19, 2019.

(51) Int. Cl.
*G06T 7/00* (2017.01)
*A61B 90/20* (2016.01)
*G01N 1/30* (2006.01)

(52) U.S. Cl.
CPC .............. *G06T 7/0012* (2013.01); *G01N 1/30* (2013.01); *A61B 90/20* (2016.02);
(Continued)

(58) Field of Classification Search
CPC ......... G06T 7/0012; G06T 2207/10056; G06T 2207/10064; G06T 2207/20081;
(Continued)

(56) References Cited

U.S. PATENT DOCUMENTS

2010/0073103 A1* 3/2010 Spears ................. H04B 1/0458
333/17.3
2014/0356897 A1* 12/2014 Wang ..................... G01N 21/33
600/407
(Continued)

FOREIGN PATENT DOCUMENTS

CN 107003242 A 8/2017
CN 107202780 A 9/2017
(Continued)

OTHER PUBLICATIONS

Rivenson et al., Virtual histological staining of unlabelled tissue-autofluorescence images via deep learning, Mar. 2019, Nature of Medical Engineering, Nature Publishing Group UK, London, vol. 3, No. 6 (Year: 2019).*
(Continued)

*Primary Examiner* — Wednel Cadeau
(74) *Attorney, Agent, or Firm* — S&F/WEHRW

(57) ABSTRACT

A computer-implemented method (530), system (100, 201) and computer readable medium for generating a slide-free histological image in the form of a reconstructed ultraviolet-based autofluorescence microscopy (UV-AutoM) image from a plurality of speckle-illuminated low-resolution images. A computer implemented method (1150), system (100, 201) and computer readable medium for generating a
(Continued)

slide-free histological image in the form of a pseudo-hematoxylin and eosin (H&E) stained image (1120) from a grayscale input image such as a UV-AutoM image or a ultraviolet-based photoacoustic microscopy (UV-PAM) image (1110).

14 Claims, 26 Drawing Sheets

(52) U.S. Cl.
    CPC .............. *G01N 2001/302* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01)

(58) Field of Classification Search
    CPC . G06T 2207/20084; G06T 2207/30024; A61B 90/20
    See application file for complete search history.

(56) References Cited

U.S. PATENT DOCUMENTS

| | | | |
|---|---|---|---|
| 2016/0077007 A1 | 3/2016 | Demos et al. | |
| 2019/0333199 A1* | 10/2019 | Ozcan | G06T 5/70 |
| 2020/0073103 A1* | 3/2020 | Wang | G01N 21/1702 |
| 2020/0175328 A1* | 6/2020 | Bonakdar Sakhi | G06T 7/0014 |
| 2021/0383538 A1* | 12/2021 | Deasy | G06T 3/4053 |

FOREIGN PATENT DOCUMENTS

| | | | | |
|---|---|---|---|---|
| KR | 2021032252 A | * | 3/2021 | ........... G02B 21/361 |
| WO | 2019154987 A1 | | 8/2019 | |
| WO | 2019191697 A1 | | 10/2019 | |

OTHER PUBLICATIONS

Jun-Yan Zhu et al., Unpaired Image-to-Image Using Cycle-Consistent Adversarial Networks, 2017, IEEE (Year: 2017).*

Rivenson et al., Virtual histological staining of unlabelled tissue-autofluorescence images via deep learning, Mar. 2019, IEEE. (Year: 2019).*

Bevin Lin et al., Clinical Translation of UV Autofluorescence Microscopy towards Endomicroscopy for Early Detection of Cancer, 2010 IEEE.

Jun-Yan Zhu et al., Unpaired Image-to-Image Translation using Cycle-Consistent Adversarial Networks, 2017 IEEE.

Office Action of JP2022-517980 issued from the Japanese Patent Office on Apr. 24, 2023.

Tu et al.; Stain-free histopathology by programmable supercontinuum pulses; Nature Photonics; 2016; vol. 10; pp. 534-540.

Orringer et al.; Rapid intraoperative histology of unprocessed surgical specimens via fibre-laser-based stimulated Raman scattering microscopy; Nature Biomedical Engineering; 2017; vol. 1; Article No. 0027.

Glaser et al.; Light-sheet microscopy for slide-free non-destructive pathology of large clinical specimens; Nature Biomedical Engineering; 2017; vol. 1; Article No. 0084.

Fereidouni et al.; Microscopy with ultraviolet surface excitation for rapid slide-free histology; Nature Biomedical Engineering; 2017; vol. 1; pp. 957-966.

Wong et al.; Fast label-free multilayered histology-like imaging of human breast cancer by photoacoustic microscopy; Science Advances; 2017; vol. 3; Issue 5; e1602168.

Rivenson et al.; Virtual histological staining of unlabelled tissue-autofluorescence images via deep learning; Nature Biomedical Engineering; 2019; vol. 3; pp. 466-477.

Rivenson et al.; PhaseStain: the digital staining of label-free quantitative phase microscopy images using deep learning; Light: Science & Applications; 2019; vol. 8, Article No. 23.

Extended European Search Report of EP application No. 20865564.7 issued from European Patent Office (EPO) on Oct. 30, 2023.

Imai Toru et al, High-throughput ultraviolet photoacoustic microscopy with multifocal excitation, Journal of Biomedical Optics, Mar. 1, 2018, p. 36007, vol. 23(3), XP060138404, ISSN: 1083-3668, DOI: 10.1117/1.JBO.23.3.036007.

Office Action of CN 202080063496.0 issued from the China National Intellectual Property Administration (CNIPA) on Mar. 6, 2025.

* cited by examiner

Reconstruction Framework

1. Input: Captured a sequence of speckle-illuminated LR images $I_j$ ($j = 1, 2, ..., N$) scanned at different positions
2. Output: High-resolution object $o(x, y)$ and unknown speckle pattern $p(x, y)$
3. Calculate object scanning trajectory $(x_j, y_j)$
4. Initialize $o(x, y)$ by interpolation of the averaged speckle images
5. for $iter = 1 : iteration$
6.    for $j = 1 : N$
7.       $\varphi_j(x, y) = o(x - x_j, y - y_j) * p(x, y)$
8.       $\psi_j(k_x, k_y) = F\big(\varphi_j(x, y)\big) * OTF(k_x, k_y)$
9.       $F\big(\varphi_j^{update}\big) = F(\varphi_j) + \alpha * conj(OTF) * [F(I_j) - \psi_j]/|OTF|^2_{max}$
10.      $o(x - x_j, y - y_j) = o(x - x_j, y - y_j) + conj(p) * (\varphi_j^{update} - \varphi_j)/|p|^2_{max}$
11.      $p = p + conj(o) * (\varphi_j^{update} - \varphi_j)/|o|^2_{max}$
12.      $loss_j = \sum_j |I_j - F^{-1}(\psi_j)|$
13.      Nesterov momentum acceleration
14.    end
15.    $\alpha = \alpha/2$ when $(loss_{j-1} - loss_j)/loss_{j-1} \leq 0.01$
16.    break when $\alpha = 0$
17. end

FIGURE 5D

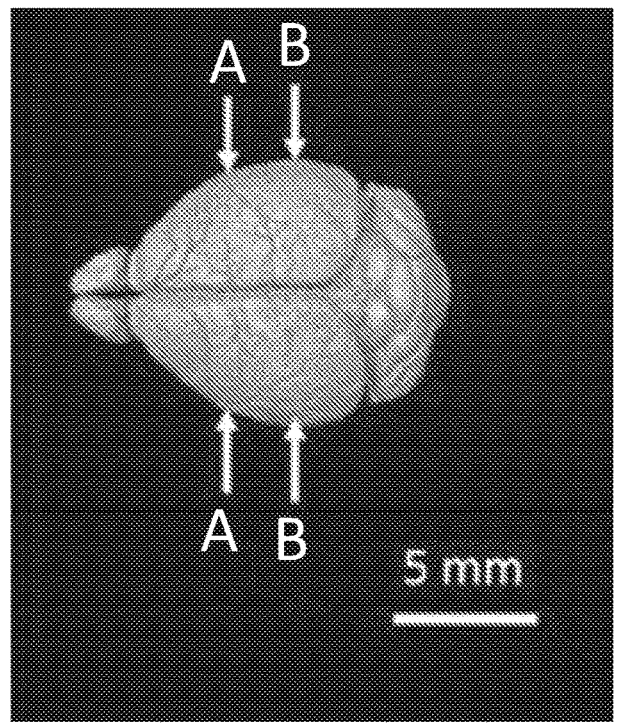
FIGURE 10A
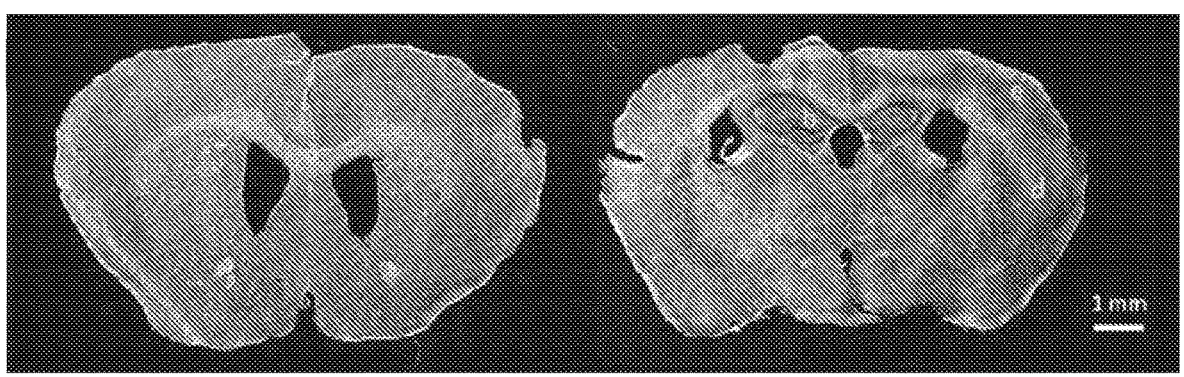
FIGURE 10B FIGURE 10C

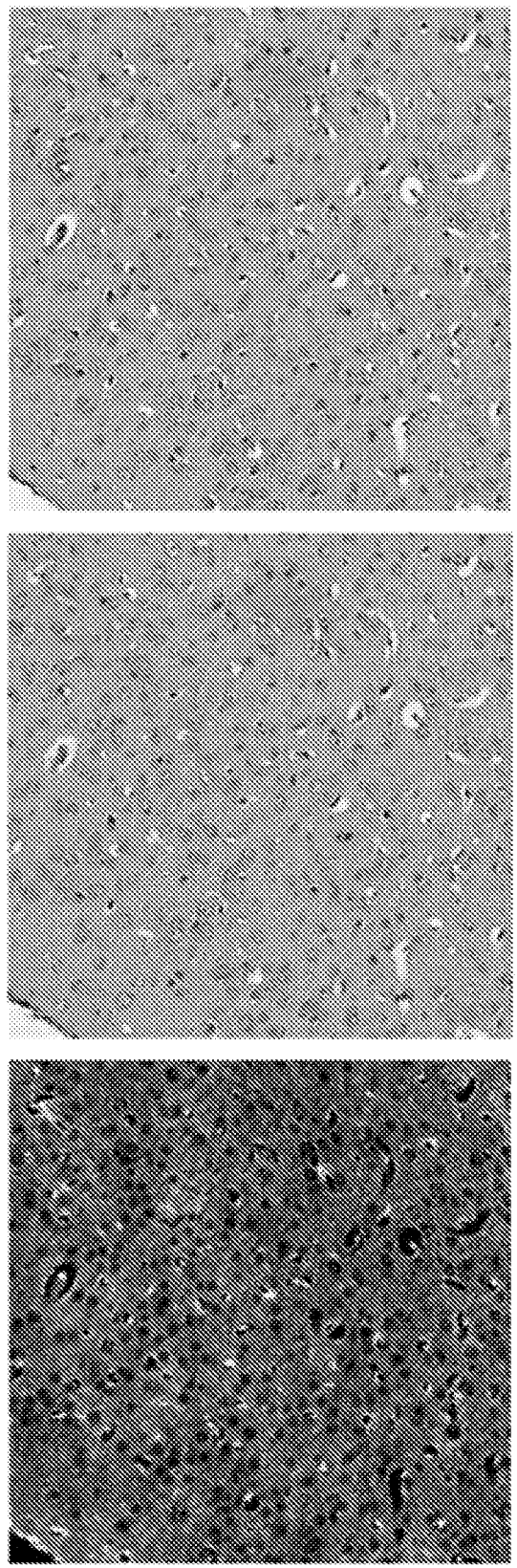

SLIDE-FREE HISTOLOGICAL IMAGING METHOD AND SYSTEM

RELATED APPLICATIONS

The current application claims priority from U.S. Provisional Patent Application No. 62/973,101 filed Sep. 19, 2019, the contents of which is herein incorporated by reference in its entirety.

TECHNICAL FIELD

The present invention relates to a slide-free histological imaging method and system.

BACKGROUND

Histological examination remains the gold standard for surgical margin assessment of malignant tumor. However, routine histological analysis, which involves a lengthy and costly procedure for sample preparation, generates toxic reagent wastes, exhausts small specimens, and prolongs the generation of histopathological reports ranging from hours to days. This lengthy and costly procedure includes formalin-fixed and paraffin-embedding (FFPE), followed by high-quality sectioning, staining, and subsequently mounting of the specimens on glass slides. These unavoidable steps require several days to accomplish, causing a delay in generating accurate diagnostic reports ranging from hours to days. Although intraoperative frozen sectioning offers a faster alternative to FFPE histology by freezing fresh tissue prior to physical sectioning, intraoperative frozen sectioning still takes 20 to 30 minutes for preparation and turnaround. Moreover, frozen sectioned specimens suffer from inherent freezing artifacts especially when dealing with lipid-rich tissues, leading to intraoperative misinterpretations and diagnostic pitfalls.

The great demand in histopathology has inspired many efforts in achieving a rapid and non-invasive diagnosis of unstained fresh tissue. Certain microscopy techniques for imaging non-sectioned tissue, including microscopy with ultraviolet (UV) surface excitation, confocal laser scanning microscopy, and light-sheet microscopy, reduce the laborious tasks and treatment costs involved in the preparation of hundreds of glass slides in conventional FFPE histology. However, these methods all require specific fluorescence labeling to improve molecular specificity. Fluorescence imaging, whilst undoubtedly powerful for providing information on morphology and dynamics of different biomolecules in cells, can lead to the use of exogenous labels or gene transfection which interfere with cell metabolism and adversely affect subsequent clinical implementations. Moreover, long term monitoring of cells with fluorescence labelling can cause photo-toxicity to cells and photo-bleaching of fluorophores themselves.

Stimulated Raman scattering (SRS) and coherent anti-Stokes Raman scattering (CARS), in which image structures are characterized by intrinsic molecular vibration of a specific chemical bond, offer a label-free alternative for the examination of C-H stretches in lipid-rich structures. Moreover, non-linear processes originated from a non-centrosymmetric interface, including second-harmonic generation (SHG), third-harmonic generation (THG), and their combined modalities, which have demonstrated significant potential for intrinsic characterization of collagen and microtubule structures. However, these methods all require a high-power ultrafast laser to maintain detection sensitivity and molecular contrast, which may not be readily available in most settings. Spectral confocal reflectance microscopy allows label-free high-resolution in vivo imaging of myelinated axons, but still requires a confocal microscope with tunable wavelength capabilities due to the low molecular specificity. Quantitative phase imaging techniques also offer great possibilities for fast refractive-index mapping through the measurement of phase variations in unstained specimens. However, they are mostly integrated into transmission systems and strictly limited by the sample thickness. In addition, reflectance-based imaging techniques such as optical coherence tomography have been translated into intraoperative diagnosis tools for label-free imaging of human breast tissue, however, it is not designed to achieve subcellular resolution and not suitable for probing molecular targets as desired in standard-of-care clinical pathology.

SUMMARY

It is an object of the present invention to address one or more disadvantages described above or herein, or at least provide a useful alternative.

In a first aspect there is provided a computer-implemented method of generating a pseudo-hematoxylin and eosin (H&E) stained image, wherein the method includes: receiving an input image, the input image being an ultraviolet-based autofluorescence microscopy (UV-AutoM) image or an ultraviolet-based photoacoustic microscopy (UV-PAM) image of an unlabeled specimen, wherein the input image is a grayscale image; transforming the input image, using the generative adversarial network, to a pseudo-H&E stained image of the input image; and outputting the pseudo-H&E stained image.

In certain implementations, the generative adversarial network is a generative adversarial network with cycle consistency.

In certain implementations, the method includes training the generative adversarial network using unpaired input and H&E stained images.

In certain implementations, the generative adversarial network comprises of four deep convolutional neural networks including: a first generator deep convolutional neural network configured to transform the input image to a generated H&E image; a second generator deep convolutional neural network configured to transform a H&E image to a generated UV-AutoM or UV-PAM image; a first discriminator deep convolutional neural network configured to discriminate between a H&E image of a training set and a generated H&E image generated by the first generator deep convolutional neural network; and a second discriminator deep convolutional neural network configured to discriminate between a UV-AutoM or UV-PAM image of the training set and a generated UV-AutoM or UV-PAM image generated by the second generator deep convolutional neural network.

In certain implementations, the first and second generator deep convolutional neural networks are ResNet-based or U-Net-based generator networks.

In certain implementations, the first and second discriminator deep convolutional neural networks are PatchGAN discriminator networks.

In certain implementations, the input image received in the form of the UV-PAM image is generated by: controlling a galvo-mirror scanner of a focusing assembly to focus ultraviolet light on a specimen according to a scanning trajectory; receiving, by at least one transducer, photoacoustic waves emitted by the specimen in response to the ultraviolet light; and generating, based on the photoacoustic waves, the UV-PAM image.

In certain implementations, the input image received in the form of a UV-AutoM image is an estimated UV-AutoM image generated from a sequence of speckle illuminated images captured according to a scanning trajectory, wherein the estimated UV-AutoM image has a higher resolution compared to each speckle illuminated image of the sequence.

In certain implementations, the estimated UV-AutoM image is generated by: a) initializing a high resolution image object based on interpolating an average of the sequence of speckle illuminated images; b) for each speckle illuminated image of the sequence: i) generate the estimated speckle illuminated image by computationally shifting the high resolution image object to a specific position in the scanning trajectory; ii) determine a filtered object-pattern compound in the frequency domain based on the estimated speckle illuminated image in the frequency domain and optical transfer function; iii) determine an updated estimated speckle illuminated image in the frequency domain based on the estimated speckle illuminated image in the frequency domain, the respective captured speckle illuminated image in the frequency domain, the filtered object pattern compound in the frequency domain, and the optical transfer function; iv) updating the high resolution object based on the updated estimated speckle illuminated image, the estimated speckle illuminated image in the spatial domain, and the speckle pattern; v) updating the speckle pattern based on the updated estimated speckle illuminated image, the estimated speckle illuminated image, and the high resolution image object; vi) applying Nesterov momentum acceleration to the high resolution image object and the speckle pattern; and c) iteratively performing step b) until convergence of reconstructing the high resolution image object is detected, the high resolution image object being the estimated UV-AutoM image with enhanced subcellular resolution across centimeter-scale imaging area.

In a second aspect there is provided a computer system configured to generate a pseudo-hematoxylin and eosin (H&E) stained image, wherein the computer system includes one or more memories having stored therein executable instructions, and one or more processors, wherein execution of the executable instructions by the processor cause the processor to: receive an input image, the input image being an ultraviolet-based autofluorescence microscopy (UV-AutoM) image or an ultraviolet-based photoacoustic microscopy (UV-PAM) image of an unlabeled specimen, wherein the input image is a grayscale image; transform the input image, using the generative adversarial network, to a pseudo-H&E stained image of the input image; and output the pseudo-H&E stained image.

In certain implementations, the generative adversarial network is a generative adversarial network with cycle consistency.

In certain implementations, the one or more processors are configured to train the generative adversarial network using unpaired input grayscale image and H&E stained images.

In certain implementations, the generative adversarial network comprises of four deep convolutional neural networks including: a first generator deep convolutional neural network configured to transform the input image to a generated H&E image; a second generator deep convolutional neural network configured to transform a H&E image to a generated UV-AutoM or UV-PAM image; a first discriminator deep convolutional neural network configured to discriminate between a H&E image of a training set and a generated H&E image generated by the first generator deep convolutional neural network; and a second discriminator deep convolutional neural network configured to discriminate between a UV-AutoM or UV-PAM image of the training set and a generated UV-AutoM or UV-PAM image generated by the second generator deep convolutional neural network.

In certain implementations, the first and second generator deep convolutional neural networks are ResNet-based or U-Net-based generator networks.

In certain implementations, the first and second discriminator deep convolutional neural networks are PatchGAN discriminator networks.

In certain implementations, the input image received in the form of the UV-PAM image is generated by: controlling a galvo-mirror scanner of a focusing assembly to focus ultraviolet light on a specimen according to a scanning trajectory; receiving, by at least one transducer, photoacoustic waves emitted by the specimen in response to the ultraviolet light; and generating, based on the photoacoustic waves, the UV-PAM image.

In certain implementations, the input image received in the form of an estimated UV-AutoM image generated from a sequence of speckle illuminated images captured according to a scanning trajectory, wherein the estimated UV-AutoM image has a higher resolution compared to each speckle illuminated image of the sequence.

In certain implementations, the estimated UV-AutoM image is generated by: a) initializing a high resolution image object based on interpolating an average of the sequence of speckle illuminated images; b) for each speckle illuminated image of the sequence: i) generate the estimated speckle illuminated image by computationally shifting the high resolution image to a specific position in the scanning trajectory; ii) determine a filtered object-pattern compound in the frequency domain based on the estimated speckle illuminated image in the frequency domain, and an optical transfer function; iii) determine an updated estimated speckle illuminated image in the frequency domain based on the estimated speckle illuminated image in the frequency domain, the respective captured speckle illuminated image in the frequency domain, the filtered object pattern compound in the frequency domain, and the optical transfer function; iv) updating the high resolution object based on the updated estimated speckle illuminated image, the estimated speckle illuminated image in the spatial domain, and the speckle pattern; v) updating the speckle pattern based on the updated estimated speckle illuminated image, the estimated speckle illuminated image, and the high resolution image object; vi) applying Nesterov momentum acceleration to the high resolution image object and the speckle pattern; and c) iteratively performing step b) until convergence of reconstructing the high resolution image object is detected, the high resolution image object being the estimated UV-AutoM image with enhanced subcellular resolution across centimeter-scale imaging area.

In a third aspect there is provided one or more non-transitory computer readable mediums including executable instructions which configure a computer system to generate a pseudo-hematoxylin and eosin (H&E) stained image, wherein the computer system has one or more processor, wherein execution of the executable instructions by the one or more processors configure the computer system to: receive an input image, the input image being an ultraviolet-based autofluorescence microscopy (UV-AutoM) image or an ultraviolet-based photoacoustic microscopy (UV-PAM) image of an unlabeled specimen, wherein the input image is a grayscale image; transform the input image, using the generative adversarial network, to a pseudo-H&E stained image of the input image; and output the pseudo-H&E stained image.

In certain implementations, the generative adversarial network is a generative adversarial network with cycle consistency.

In certain implementations, the execution of the executable instructions by the one or more processors configure the computer system to train the generative adversarial network using unpaired input grayscale image and H&E stained images.

In certain implementations, the generative adversarial network comprises of four deep convolutional neural networks including: a first generator deep convolutional neural network configured to transform the input image to a generated H&E image; a second generator deep convolutional neural network configured to transform a H&E image to a generated UV-AutoM or UV-PAM image; a first discriminator deep convolutional neural network configured to discriminate between a H&E image of a training set and a generated H&E image generated by the first generator deep convolutional neural network; and a second discriminator deep convolutional neural network configured to discriminate between a UV-AutoM or UV-PAM image of the training set and a generated UV-AutoM or UV-PAM image generated by the second generator deep convolutional neural network.

In certain implementations, the first and second generator deep convolutional neural networks are ResNet-based or U-Net-based generator networks.

In certain implementations, the first and second discriminator deep convolutional neural networks are PatchGAN discriminator networks.

In certain implementations, the input image received in the form of the UV-PAM image is generated by: controlling a galvo-mirror scanner of a focusing assembly to focus ultraviolet light on a specimen according to a scanning trajectory; receiving, by at least one transducer, photoacoustic waves emitted by the specimen in response to the ultraviolet light; and generating, based on the photoacoustic waves, the UV-PAM image.

In certain implementations, the input image received in the form of an estimated UV-AutoM image generated from a sequence of speckle illuminated images captured according to a scanning trajectory, wherein the estimated UV-AutoM image has a higher resolution compared to each speckle illuminated image of the sequence.

In certain implementations, the UV-AutoM image is generated by the one or more processors by: a) initializing a high resolution image object based on interpolating an average of the sequence of speckle illuminated images; b) for each speckle illuminated image of the sequence: i) generate the estimated speckle illuminated image by computationally shifting the high resolution image to a specific position in the scanning trajectory; ii) determine a filtered object-pattern compound in the frequency domain based on the estimated speckle illuminated image in the frequency domain, and an optical transfer function; iii) determine an updated estimated speckle illuminated image in the frequency domain based on the estimated speckle illuminated image in the frequency domain, the respective captured speckle illuminated image in the frequency domain, the filtered object pattern compound in the frequency domain, and the optical transfer function; iv) updating the high resolution object based on the updated estimated speckle illuminated image, the estimated speckle illuminated image in the spatial domain, and the speckle pattern; v) updating the speckle pattern based on the updated estimated speckle illuminated image, the estimated speckle illuminated image, and the high resolution image object; and vi) applying Nesterov momentum acceleration to the high resolution image object and the speckle pattern; and c) iteratively performing step b) until convergence of reconstructing the high resolution image object is detected, the high resolution image object being the estimated UV-AutoM image with enhanced subcellular resolution across centimeter-scale imaging area.

Other aspects and embodiments will be appreciated throughout the description of the embodiments.

BRIEF DESCRIPTION OF DRAWINGS

Preferred embodiments of the present invention will now be described, by way of examples only, with reference to the accompanying drawings.

FIG. 5D is an example of the pseudocode representing the computer-implemented method of reconstructing a UV-AutoM image through a sequence of speckle-illuminated low-resolution images.

FIG. 10A is an example image of a top view of a mouse brain.

FIGS. 10B and 10C are examples of reconstructed UV-AutoM images each depicting a cross-sectional cut through Lines A-A and B-B of the mouse brain of FIG. 10A.

FIG. 15A is an example of a UV-AutoM image of a deparaffinized FFPE mouse brain section with 7-µm thickness.

FIG. 15B is a virtual stained version of the UV-AutoM image of FIG. 15A utilizing a GAN based network.

FIG. 15C is a bright-field H&E image of the mouse brain section imaged in relation to FIG. 15A.

DESCRIPTION OF EMBODIMENTS

Figure 1A:
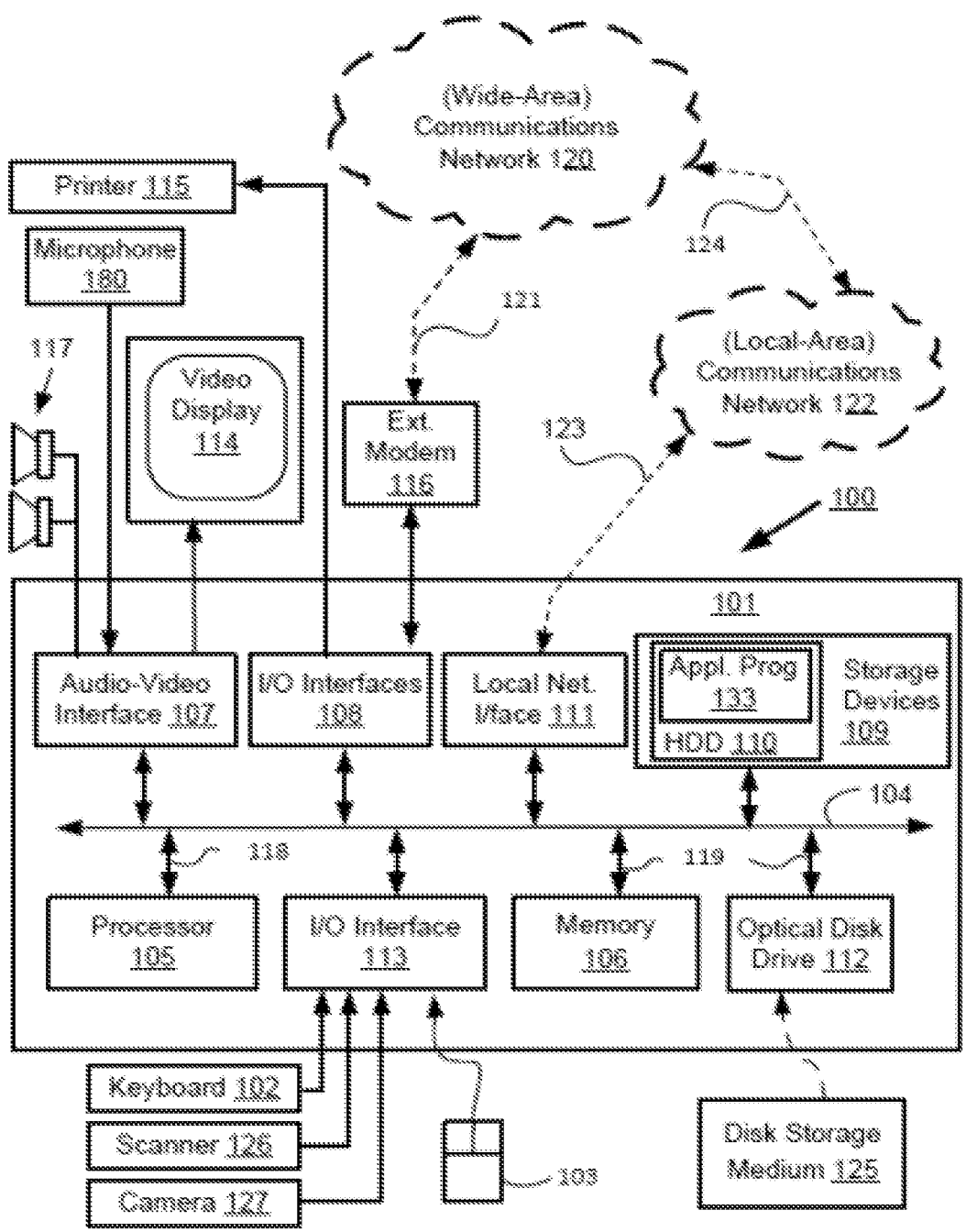
FIGS. 1A and 1B are schematics of an example of a general-purpose computer system upon which various arrangements described herein are implemented.

Where reference is made in any one or more of the accompanying drawings to steps and/or features, which have the same reference numerals, those steps and/or features have for the purposes of this description the same function(s) or operation(s), unless the contrary intention appears.

It is to be noted that the discussions contained in the "Background" section and that above relating to prior art arrangements relate to discussions of documents or devices which form public knowledge through their respective publication and/or use. Such should not be interpreted as a representation by the present inventor(s) or the patent applicant that such documents or devices in any way form part of the common general knowledge in the art.

Figure 1B:
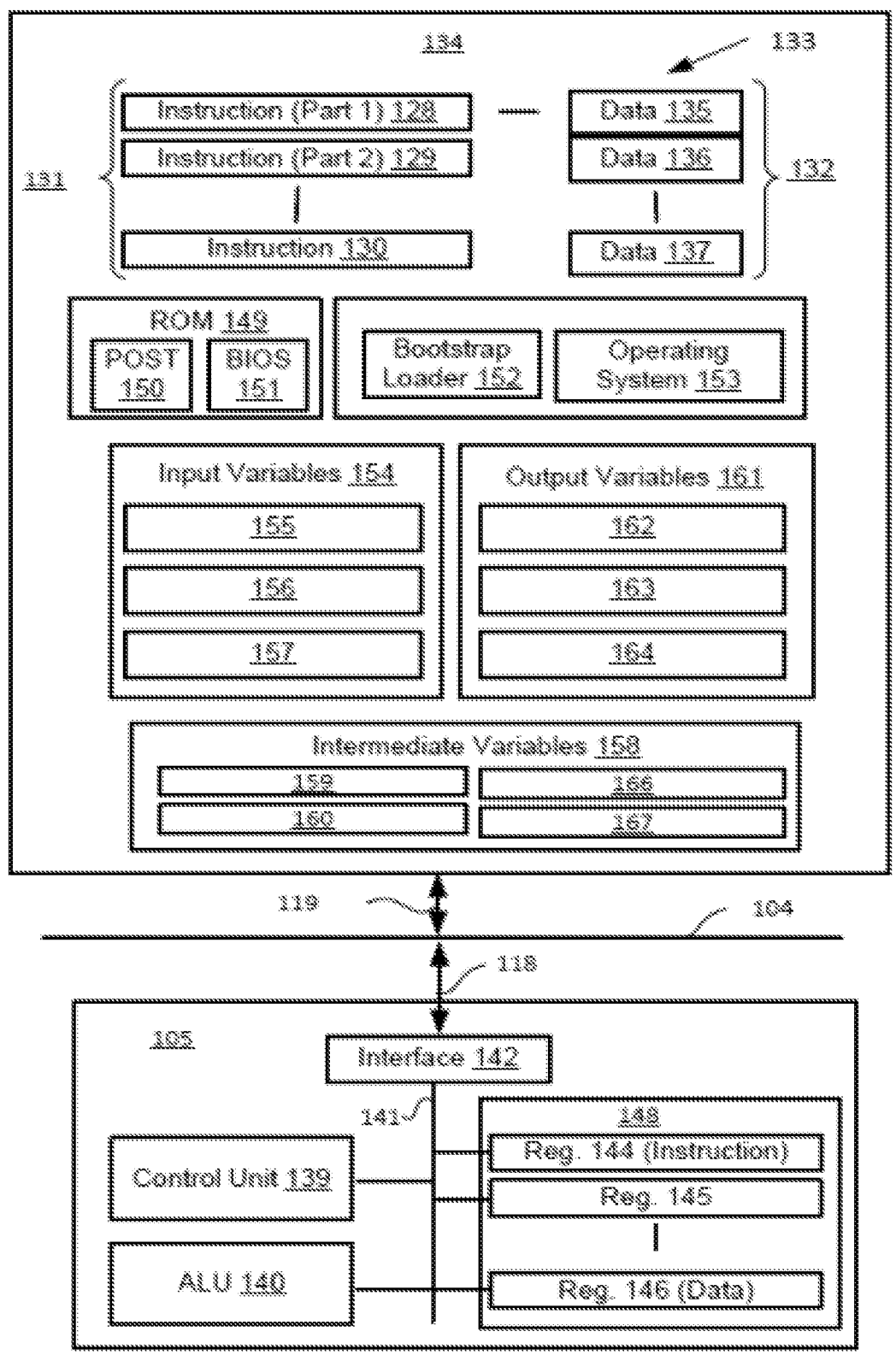

Referring to FIGS. 1A and 1B there is shown a schematic of an example of a general-purpose computer system 100, upon which the various arrangements described herein.

As seen in FIG. 1A, the computer system 100 includes: a computer module 101; input devices such as a keyboard 102, a mouse pointer device 103, a scanner 126, a camera 127, and a microphone 180; and output devices including a printer 115, a display device 114 and loudspeakers 117. An external Modulator-Demodulator (Modem) transceiver device 116 may be used by the computer module 101 for communicating to and from a communications network 120 via a connection 121. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer module 101 typically includes at least one processor unit 105, and a memory unit 106. For example, the memory unit 106 may have semiconductor random access memory (RAM) and semiconductor read only memory (ROM). The computer module 101 also includes an number of input/output (I/O) interfaces including: an audio-video interface 107 that couples to the video display 114, loudspeakers 117 and microphone 180; an 1/O interface 113 that couples to the keyboard 102, mouse 103, scanner 126, camera 127 and optionally a joystick or other human interface device (not illustrated), or a projector; and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may comprise an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial and parallel connectivity, the former typically being implemented according to the Universal Serial Bus (USB) standards and having corresponding USB connectors (not illustrated). Storage devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD- ROM, DVD, Blu ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119. Examples of computers on which the described arrangements can be practiced include IBM-PC's and compatibles, Sun Sparcstations, Apple Mac™ or a like computer system.

The methods as described herein may be implemented using the computer system 100 wherein the processes described herein may be implemented as one or more software application programs 133 executable within the computer system 100. In particular, the steps of the methods described herein are effected by instructions 131 (see FIG. 1B) in the software 133 that are carried out within the computer system 100. The software instructions 131 may be formed as one or more code modules, each for performing one or more particular tasks.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. The use of the computer program product in the computer system 100 preferably effects an advantageous apparatus for detecting and/or sharing writing actions.

The software 133 is typically stored in the HDD 110 or the memory 106. The software is loaded into the computer system 100 from a computer readable medium, and executed by the computer system 100. Thus, for example, the software 133 may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit. USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. Through manipulation of typically the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 executes. The POST program 150 is typically stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 activates the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source across one of the networks 120, 102, data retrieved from one of the storage devices 106, 109 or data retrieved from the storage medium 125 inserted into the corresponding reader 112, all depicted in FIG. 1A. The execution of a set of the instructions may in some cases result in output of data. Execution may also involve storing data or variables to the memory 134.

The disclosed writing detection and sharing arrangements use input variables 154, which are stored in the memory 134 in corresponding memory locations 155, 156, 157. The writing detection and sharing arrangements produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle comprises: a fetch operation, which fetches or reads an instruction 131 from a memory location 128, 129, 130; a decode operation in which the control unit 139 determines which instruction has been fetched; and an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 162.

Each step or sub-process in the processes described herein are associated with one or more segments of the program 133 and is performed by the register section 144, 145, 147, the ALU 140, and the control unit 139 in the processor 105 working together to perform the fetch, decode, and execute cycles for every instruction in the instruction set for the noted segments of the program 133.

The methods described herein may alternatively be implemented in dedicated hardware such as one or more integrated circuits performing the functions or sub functions of the writing detection and sharing methods. Such dedicated hardware may include graphic processors, digital signal processors, or one or more microprocessors and associated memories.

Figure 2A:
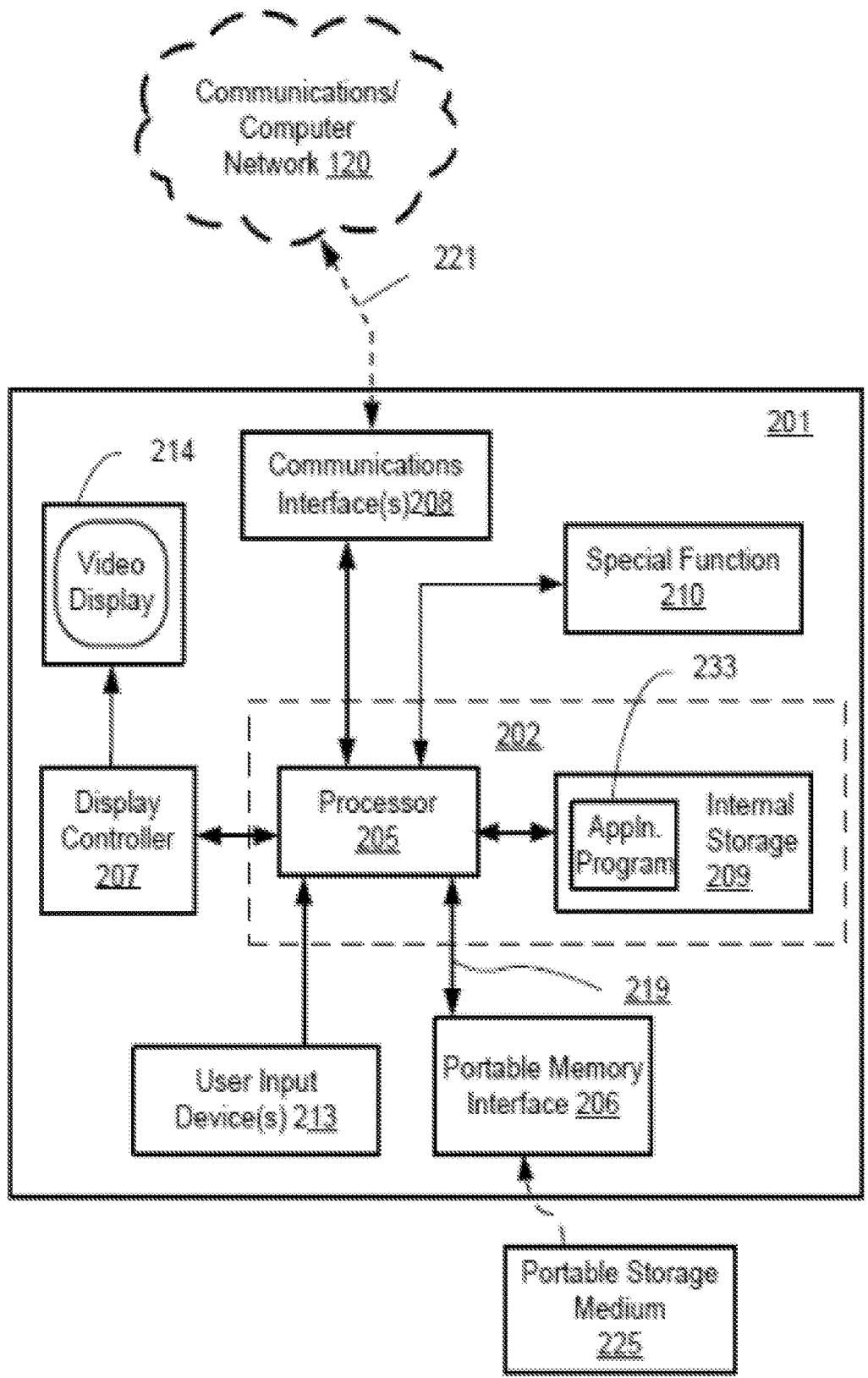
FIGS. 2A and 2B are schematics of an example of an embedded system upon which various arrangements described herein are implemented.
Figure 2B:
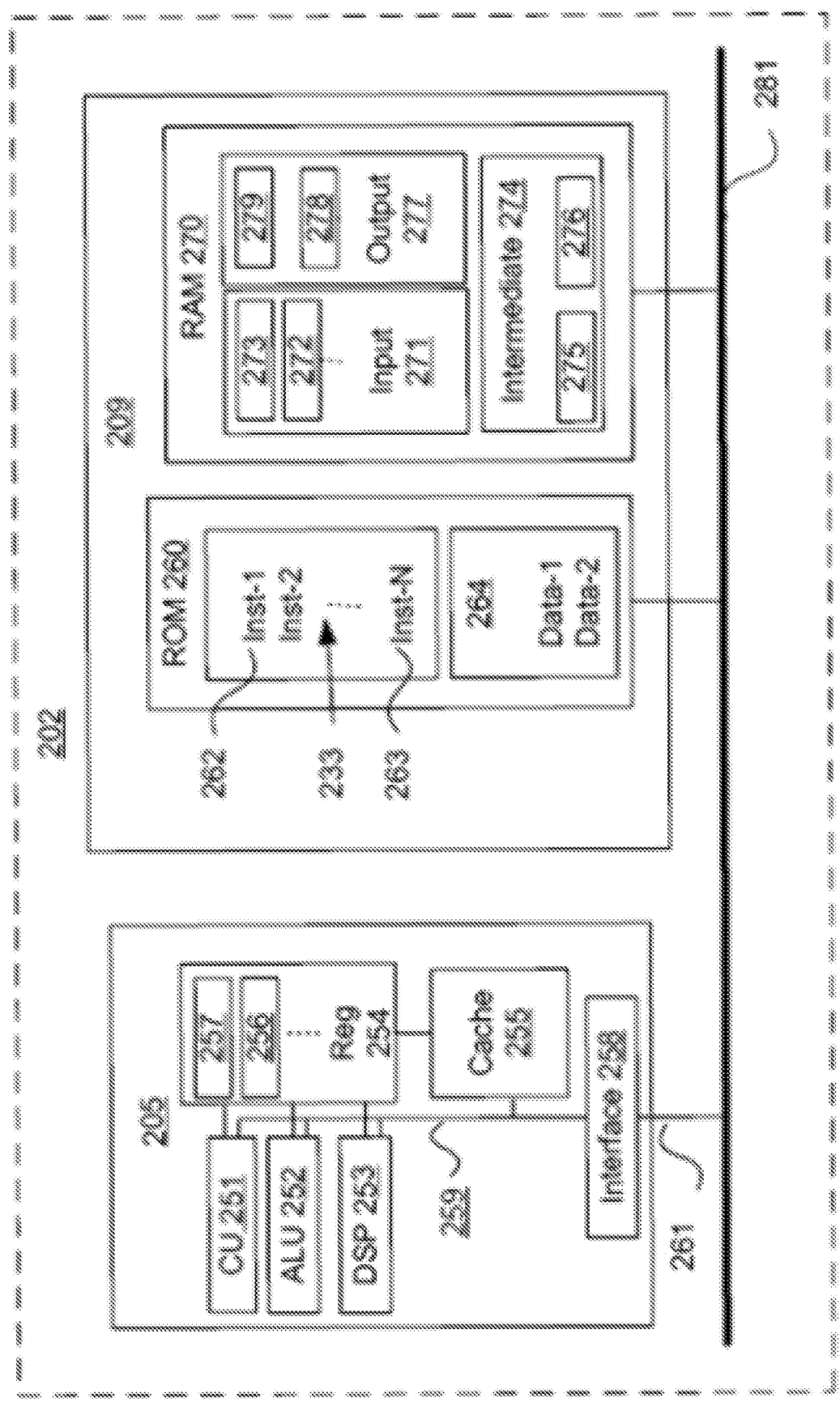

FIGS. 2A and 2B collectively form a schematic block diagram of a general purpose electronic device 201 including embedded components, upon which the writing detection and/or sharing methods to be described are desirably practiced. The electronic device 201 may be, for example, a mobile phone, a portable media player, virtual reality glasses or a digital camera, in which processing resources are limited. Nevertheless, the methods to be described may also be performed on higher-level devices such as desktop computers, server computers, and other such devices with significantly larger processing resources.

As seen in FIG. 2A, the electronic device 201 comprises an embedded controller 202. Accordingly, the electronic device 201 may be referred to as an "embedded device." In the present example, the controller 202 has a processing unit (or processor) 205 which is bi-directionally coupled to an internal storage module 209. The storage module 209 may be formed from non-volatile semiconductor read only memory (ROM) 260 and semiconductor random access memory (RAM) 270, as seen in FIG. 2B. The RAM 270 may be volatile, non-volatile or a combination of volatile and non-volatile memory.

The electronic device 201 includes a display controller 207, which is connected to a display 214, such as a liquid crystal display (LCD) panel or the like. The display controller 207 is configured for displaying graphical images on the display 214 in accordance with instructions received from the embedded controller 202, to which the display controller 207 is connected.

The electronic device 201 also includes user input devices 213 which are typically formed by keys, a keypad or like controls. In some implementations, the user input devices 213 may include a touch sensitive panel physically associated with the display 214 to collectively form a touch-screen. Such a touch-screen may thus operate as one form of graphical user interface (GUI) as opposed to a prompt or menu driven GUI typically used with keypad-display combinations. Other forms of user input devices may also be used, such as a microphone (not illustrated) for voice commands or a joystick/thumb wheel (not illustrated) for ease of navigation about menus.

As seen in FIG. 2A, the electronic device 201 also comprises a portable memory interface 206, which is coupled to the processor 205 via a connection 219. The portable memory interface 206 allows a complementary portable memory device 225 to be coupled to the electronic device 201 to act as a source or destination of data or to supplement the internal storage module 209. Examples of such interfaces permit coupling with portable memory devices such as Universal Serial Bus (USB) memory devices, Secure Digital (SD) cards, Personal Computer Memory Card International Association (PCMIA) cards, optical disks and magnetic disks.

The electronic device 201 also has a communications interface 208 to permit coupling of the device 201 to a computer or communications network 220 via a connection 221. The connection 221 may be wired or wireless. For example, the connection 221 may be radio frequency or optical. An example of a wired connection includes Ethernet. Further, an example of wireless connection includes Bluetooth™ type local interconnection, Wi-Fi (including protocols based on the standards of the IEEE 802.11 family), Infrared Data Association (IrDa) and the like.

Typically, the electronic device 201 is configured to perform some special function. The embedded controller 202, possibly in conjunction with further special function components 210, is provided to perform that special function. For example, where the device 201 is a digital camera, the components 210 may represent a lens, focus control and image sensor of the camera. The special function component 210 is connected to the embedded controller 202. As another example, the device 201 may be a mobile telephone handset.

In this instance, the components 210 may represent those components required for communications in a cellular telephone environment. Where the device 201 is a portable device, the special function components 210 may represent a number of encoders and decoders of a type including Joint Photographic Experts Group (JPEG), (Moving Picture Experts Group) MPEG, MPEG-1 Audio Layer 3 (MP3), and the like.

The methods described hereinafter may be implemented using the embedded controller 202, where the processes described herein may be implemented as one or more software application programs 233 executable within the embedded controller 202. The electronic device 201 of FIG. 2A implements the described methods. In particular, with reference to FIG. 2B, the steps of the described methods are effected by instructions in the software 233 that are carried out within the controller 202. The software instructions may be formed as one or more code modules, each for performing one or more particular tasks. The software may also be divided into two separate parts, in which a first part and the corresponding code modules performs the described methods and a second part and the corresponding code modules manage a user interface between the first part and the user.

The software 233 of the embedded controller 202 is typically stored in the non-volatile ROM 260 of the internal storage module 209. The software 233 stored in the ROM 260 can be updated when required from a computer readable medium. The software 233 can be loaded into and executed by the processor 205. In some instances, the processor 205 may execute software instructions that are located in RAM 270. Software instructions may be loaded into the RAM 270 by the processor 205 initiating a copy of one or more code modules from ROM 260 into RAM 270. Alternatively, the software instructions of one or more code modules may be pre-installed in a non-volatile region of RAM 270 by a manufacturer. After one or more code modules have been located in RAM 270, the processor 205 may execute software instructions of the one or more code modules.

The application program 233 is typically pre-installed and stored in the ROM 260 by a manufacturer, prior to distribution of the electronic device 201. However, in some instances, the application programs 233 may be supplied to the user encoded on one or more CD-ROM (not shown) and read via the portable memory interface 206 of FIG. 2A prior to storage in the internal storage module 209 or in the portable memory 225. In another alternative, the software application program 233 may be read by the processor 205 from the network 220, or loaded into the controller 202 or the portable storage medium 225 from other computer readable media. Computer readable storage media refers to any non-transitory tangible storage medium that participates in providing instructions and/or data to the controller 202 for execution and/or processing. Examples of such storage media include floppy disks, magnetic tape, CD-ROM, a hard disk drive, a ROM or integrated circuit, USB memory, a magneto-optical disk, flash memory, or a computer readable card such as a PCMCIA card and the like, whether or not such devices are internal or external of the device 201. Examples of transitory or non-tangible computer readable transmission media that may also participate in the provision of software, application programs, instructions and/or data to the device 201 include radio or infra-red transmission channels as well as a network connection to another computer or networked device, and the Internet or Intranets including e-mail transmissions and information recorded on Websites and the like. A computer readable medium having such software or computer program recorded on it is a computer program product.

The second part of the application programs 233 and the corresponding code modules mentioned above may be executed to implement one or more graphical user interfaces (GUIs) to be rendered or otherwise represented upon the display 214 of FIG. 2A. Through manipulation of the user input device 213 (e.g., the keypad), a user of the device 201 and the application programs 233 may manipulate the interface in a functionally adaptable manner to provide controlling commands and/or input to the applications associated with the GUI(s). Other forms of functionally adaptable user interfaces may also be implemented, such as an audio interface utilizing speech prompts output via loudspeakers (not illustrated) and user voice commands input via the microphone (not illustrated).

FIG. 2B illustrates in detail the embedded controller 202 having the processor 205 for executing the application programs 233 and the internal storage 209. The internal storage 209 comprises read only memory (ROM) 260 and random access memory (RAM) 270. The processor 205 is able to execute the application programs 233 stored in one or both of the connected memories 260 and 270. When the electronic device 201 is initially powered up, a system program resident in the ROM 260 is executed. The application program 233 permanently stored in the ROM 260 is sometimes referred to as "firmware". Execution of the firmware by the processor 205 may fulfil various functions, including processor management, memory management, device management, storage management and user interface.

The processor 205 typically includes a number of functional modules including a control unit (CU) 251, an arithmetic logic unit (ALU) 252, a digital signal processor (DSP) 253 and a local or internal memory comprising a set of registers 254 which typically contain atomic data elements 256, 257, along with internal buffer or cache memory 255. One or more internal buses 259 interconnect these functional modules. The processor 205 typically also has one or more interfaces 258 for communicating with external devices via system bus 281, using a connection 261.

The application program 233 includes a sequence of instructions 262 through 263 that may include conditional branch and loop instructions. The program 233 may also include data, which is used in execution of the program 233. This data may be stored as part of the instruction or in a separate location 264 within the ROM 260 or RAM 270.

In general, the processor 205 is given a set of instructions, which are executed therein. This set of instructions may be organised into blocks, which perform specific tasks or handle specific events that occur in the electronic device 201. Typically, the application program 233 waits for events and subsequently executes the block of code associated with that event. Events may be triggered in response to input from a user, via the user input devices 213 of FIG. 2A, as detected by the processor 205. Events may also be triggered in response to other sensors and interfaces in the electronic device 201.

The execution of a set of the instructions may require numeric variables to be read and modified. Such numeric variables are stored in the RAM 270. The disclosed method uses input variables 271 that are stored in known locations 272, 273 in the memory 270. The input variables 271 are processed to produce output variables 277 that are stored in known locations 278, 279 in the memory 270. Intermediate variables 274 may be stored in additional memory locations in locations 275, 276 of the memory 270. Alternatively, some intermediate variables may only exist in the registers 254 of the processor 205.

The execution of a sequence of instructions is achieved in the processor 205 by repeated application of a fetch-execute cycle. The control unit 251 of the processor 205 maintains a register called the program counter, which contains the address in ROM 260 or RAM 270 of the next instruction to be executed. At the start of the fetch execute cycle, the contents of the memory address indexed by the program counter is loaded into the control unit 251. The instruction thus loaded controls the subsequent operation of the processor 205, causing for example, data to be loaded from ROM memory 260 into processor registers 254, the contents of a register to be arithmetically combined with the contents of another register, the contents of a register to be written to the location stored in another register and so on. At the end of the fetch execute cycle the program counter is updated to point to the next instruction in the system program code. Depending on the instruction just executed this may involve incrementing the address contained in the program counter or loading the program counter with a new address in order to achieve a branch operation.

Each step or sub-process in the processes of the methods described below is associated with one or more segments of the application program 233, and is performed by repeated execution of a fetch-execute cycle in the processor 205 or similar programmatic operation of other independent processor blocks in the electronic device 201.

Aspects provide a high-throughput, label-free, and slide-free imaging method and system based on intrinsic optical absorption contrast under ultraviolet light illumination to probe histologically-stained biomolecules directly. Two approaches are disclosed, namely ultraviolet-based (i) photoacoustic microscopy (UV-PAM), and (ii) autofluorescence microscopy (UV-AutoM). To achieve high throughput for UV-PAM, a high-speed optical scanning configuration can be utilized. In relation to UV-AutoM, speckle illumination (SI) is utilized which allows estimation of high-resolution images with a low-magnification objective lens, providing images with subcellular resolution across centimeter-scale imaging area, whilst simultaneously allowing high tolerance to tissue surface morphology, slide placement errors and thickness-induced image blur.

For both types of images, UV-PAM and UV-AutoM, a deep learning-based virtual staining method and system is disclosed which can be used to generate histology-like images of large unprocessed fresh/fixed tissues at subcellular resolution. The virtual staining method and system utilizes a generative adversarial network (GAN), which is configured to enable transformation of a UV-PAM or UV-AutoM image of an unlabeled tissue into a histologically-stained image through paired/unpaired training examples. The disclosed method and system can simplify the workflow of standard-of-care histopathology from days to less than ten minutes, enabling intraoperative surgical margin assessment, thereby reducing or eliminating the need of second surgeries due to positive margin.

Ultraviolet-Based Photoacoustic Microscopy (UV-PAM)

Unlike conventional optical microscopy, PAM takes the advantage of optical absorption contrast, which is highly specific. By using a UV pulsed laser (wavelengths ranging from ~240-280 nm) as an excitation beam, cell nuclei can be highlighted, thus providing label-free histology-like images.

Figure 3:
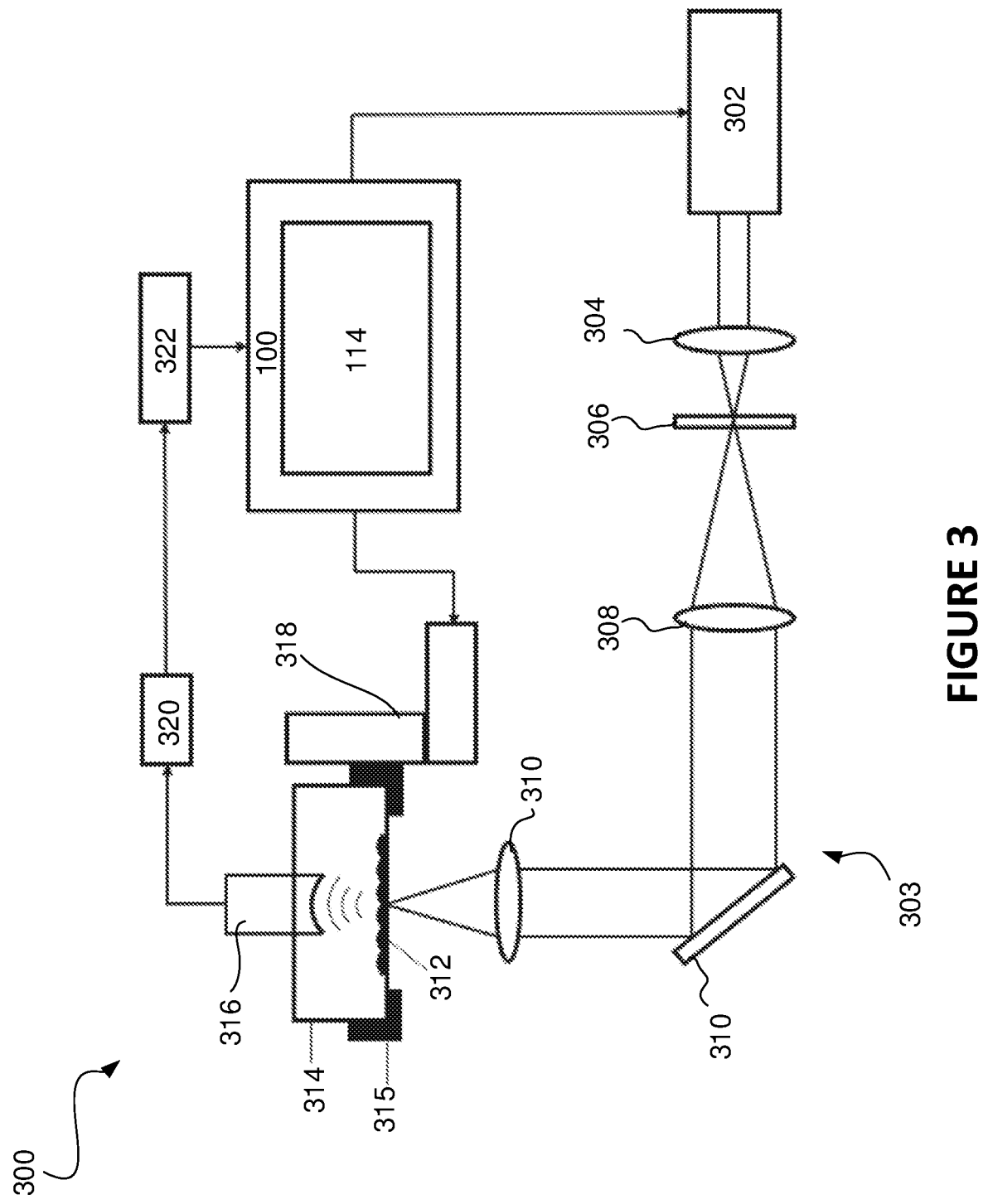
FIG. 3 is a schematic of an example UV-PAM system.

Referring to FIG. 3 there is shown an example of a UV-PAM system 300. In particular, a nanosecond pulsed UV laser 302 (for example, WEDGE-HF 266 nm, available from Bright Solution Srl.) is focused by a focusing assembly 303. In particular, the light emitted by the UV laser 302 is expanded by a pair of lenses 304, 308 (for example, LA4647-UV and LA4663-UV, available from Thorlabs Inc.). The quality of the UV light beam can be improved by a pinhole 306 located between the pair of lenses 304, 308. The size of the pinhole 306 may be 10 μm to 100 μm in diameter, (for example, P25C, available from Thorlabs Inc.). The beam is subsequently reflected by a 1D galvo-mirror scanner 310 and then focused on the bottom of a specimen 312 by an objective lens 310 (for example, a MicroSpot™ Focusing Objective (LMU-20X-UVB), Thorlabs Inc.). The specimen 312 is placed on the bottom of a water tank 314 which is held by a sample holder 315 attached to an XYZ translation stage 318. The water tank 314 is filled with water to allow the photoacoustic waves to propagate upward and to be detected by a water-immersed ultrasonic transducer 316 (for example, V324-SU, available fdrom Olympus NDT Inc.).

The received acoustic pressure is converted to electric signals, then amplified by amplifiers 320 (for example, two ZFL-500LN-BNC+, available from Mini-circuits Inc.) and last, received by a computer system 100 or 201 through a data acquisition system 322 (for example, ATS9350, available from Alazar Technologies Inc.). To generate a two-dimensional image, the maximum amplitude projection (MAP) of each A-line signal is first identified. The maximum amplitude projections are then rearranged according to the order in the scanning process to generate grayscale images.

In operation, the galvo-mirror scanner 310 of the focusing assembly can be controlled to focus ultraviolet light on the specimen 312 according to a scanning trajectory. The controlling of the galvo-mirror scanner 310 can be performed by the computer system 100 or part of a computerised embedded device 201. The transducer 316 is configured to receive the photoacoustic waves emitted by the specimen 312 in response to ultraviolet light. The computer system 100 or embedded device 201 generates, based on the photoacoustic waves, the UV-PAM image.

Figure 4A:
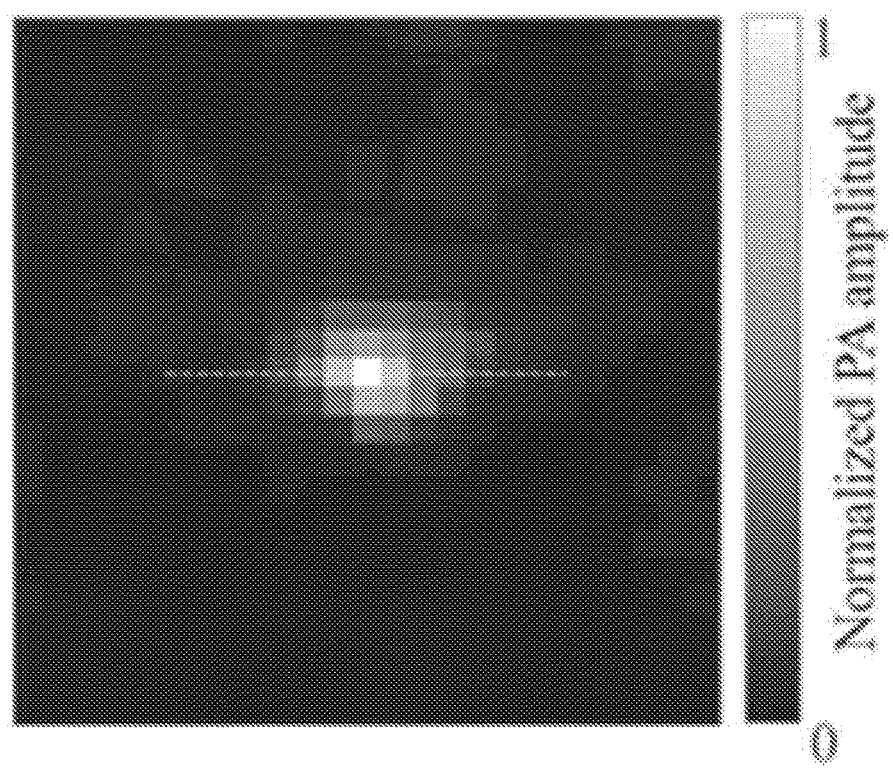
FIG. 4A is an example of a UV-PAM image of a gold nanoparticle with 200-nm diameter, wherein the profile along the white dashed line is extracted for averaging.
Figure 4B:
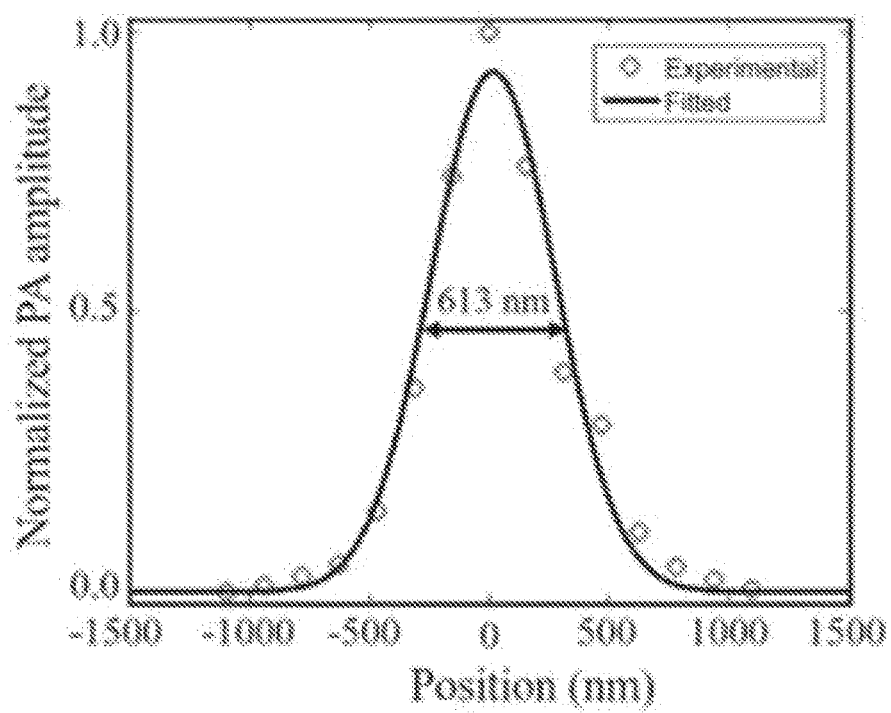
FIG. 4B is an example of an averaged line profile of four gold nanoparticles, wherein the FWHM (full width at half maximum) of the Gaussian fitting (solid line) is about 613 nm, representing the lateral resolution of the UV-PAM system of FIG. 3.
Figure 4C:
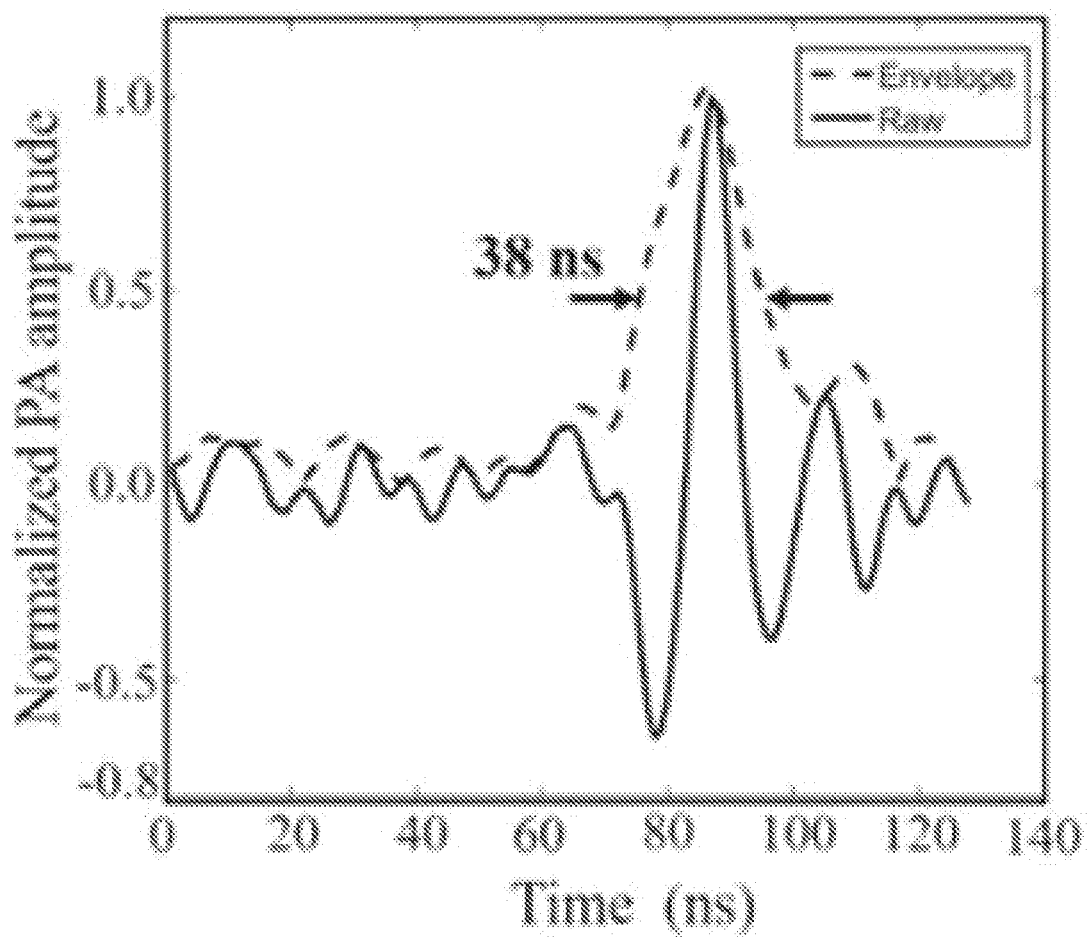
FIG. 4C is an example of an A-line signal of the central position of the gold nanoparticle in FIG. 4A, wherein the FWHM of the envelope of the A-line signal is 38 ns, which corresponds to 58 µm, representing the axial resolution of the UV-PAM system of FIG. 3.

In order to measure the lateral and axial resolutions of the UV-PAM system, gold nanoparticles (200-nm diameter) were imaged with a step size of 0.15 μm on both x- and y-axis (FIG. 4(a)). The data points of four gold nanoparticles were selected and averaged to measure the lateral resolution by Gaussian profile fitting as shown in FIG. 4(b). The full width at half maximum (FWHM) of the Gaussian fitting profile is ~0.6 μm. To evaluate the axial resolution, the envelope of the A-line signal of the central position can be extracted. FIG. 4(c) shows the A-line signal of the central position of the gold nanoparticle in (a). The FWHM of the envelope of the A-line signal is 38 ns, which corresponds to 58 μm, representing the axial resolution of the UV-PAM system.

Ultraviolet-Based Autofluorescence Microscopy (UV-AutoM)

In histopathological examination, an objective lens with a 20×-40× magnification factor is typically required to achieve a subcellular resolution for the observation of cellular morphology and metabolic activities. However, such a magnification factor restricts the field-of-view (FOV) to within 1 mm². In addition, high magnification objective lens suffers more from spatially-varied aberrations and features a shallow depth-of-field (DOF) which leads to low tolerance to placement errors of microscope slide and specimen roughness. For such reasons, capturing a large tissue surface via image stitching with a high magnification objective lens is sub-optional.

Disclosed is a speckle illumination (SI) method to alleviate inherent tradeoffs between a large FOV and high resolution (HR) in digital microscopes, enabling a high-throughput visualization of different regions of interest with subcellular resolution.

Figure 5A:
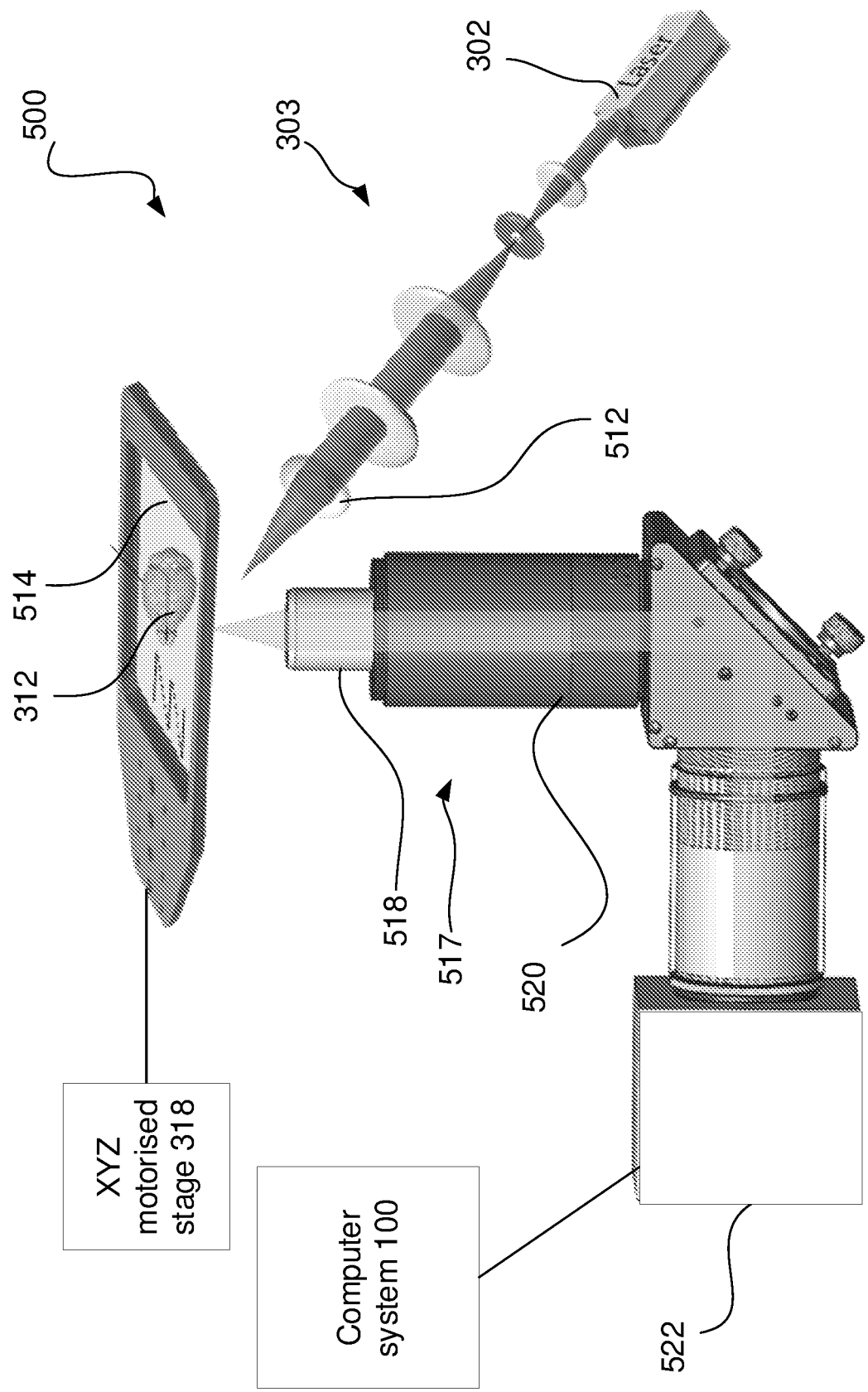
FIG. 5A is a schematic of an example UV-AutoM system.

As illustrated in FIG. 5A showing an example UV-AutoM system 500, an unstained fresh tissue 312 is placed on an open-top sample holder which is connected to an XYZ motorized stage 318 (for example, three L-509, available from PI miCos, GmbH). A UV laser 302 (for example, WEDGE-HF 266 nm, available from Bright Solution Srl.) is collimated and projected onto a fused silica diffuser (for example, DGUV10-600, available from Thorlabs Inc.) to generate a speckle pattern. The resulting wave is focused through an aspherical UV condenser lens 512 with a numerical aperture (NA) of 0.69 (for example, #33-957, available from Edmund Optics Inc.) as part of the focusing assembly 303. The sample 312 is obliquely illuminated through a UV transparent window 514 (e.g. transmission greater than 90% from 200 nm to 1500 nm). The excited autofluorescence signal (mainly from NADH and FAD, peak emission at 450 nm) is then collected by an inverted microscope 517 equipped with a 4× objective lens 518 (e.g. NA=0.1, plan achromat objective, available from Olympus NDT Inc.) and an infinity-corrected tube lens 520 (TTL180-A, available from Thorlabs Inc.), and finally imaged by a monochrome scientific complementary metal-oxide semiconductor (sC-MOS) camera 522 (for example, a PCO edge 4.2, 6.5 μm pixel pitch, available from PCO AG).

A low magnification objective lenses suffers less from spatially-varied aberrations across a large FOV, and features larger DOF and longer working distance, which allows high tolerance to slide placement errors and enables flexible operations on the sample stage. However, its spatial resolution is largely restricted by the low NA value, which is the determining factor for the achievable resolution of an imaging system according to Rayleigh criterion (i.e. the minimum distance that an imaging system can resolve is 0.61λ/NA, where X is the fluorescence emission wavelength and NA is the objective lens's numerical aperture). To this end, SI reconstruction is utilized to bypass such a resolution-limit set by a low-NA objective lens in this configuration.

Disclosed is a computational imaging method based on speckle illumination to achieve autofluorescence microscopy. In a preferred embodiment, this method achieves high-throughput microscopy. In particular, "high-throughput microscopy" refers to the use of automated microscopy and image analysis to visualize and quantitatively capture cellular features at a large scale. More specifically, the spatial-bandwidth product (i.e. field-of-view/resolution$^2$) of the high-throughput output due to the application of speckle illumination is about or equal to 10 times more than conventional fluorescence microscopy which is typically constrained to megapixels level. A low-magnification objective lens is favored for imaging large tissue surface since it suffers less from spatially-varied aberrations. In addition, out-of-focus image blur caused by surface irregularity, tissue thickness, or slide placement errors can be minimized through the implementation of a low-magnification lens since their large depth-of-field. However, the low numerical aperture (NA) value of such lens largely restricts the achievable resolution, thus hinder their applications where the target on subcellular-level imaging. The proposed method performs an iterative reconstruction through a sequence of speckle-illuminated low-resolution autofluorescence images to bypass the resolution limit set by a low-NA objective lens, facilitating fast high-resolution imaging across a large imaging area with arbitrary surface morphology.

Figure 5B:
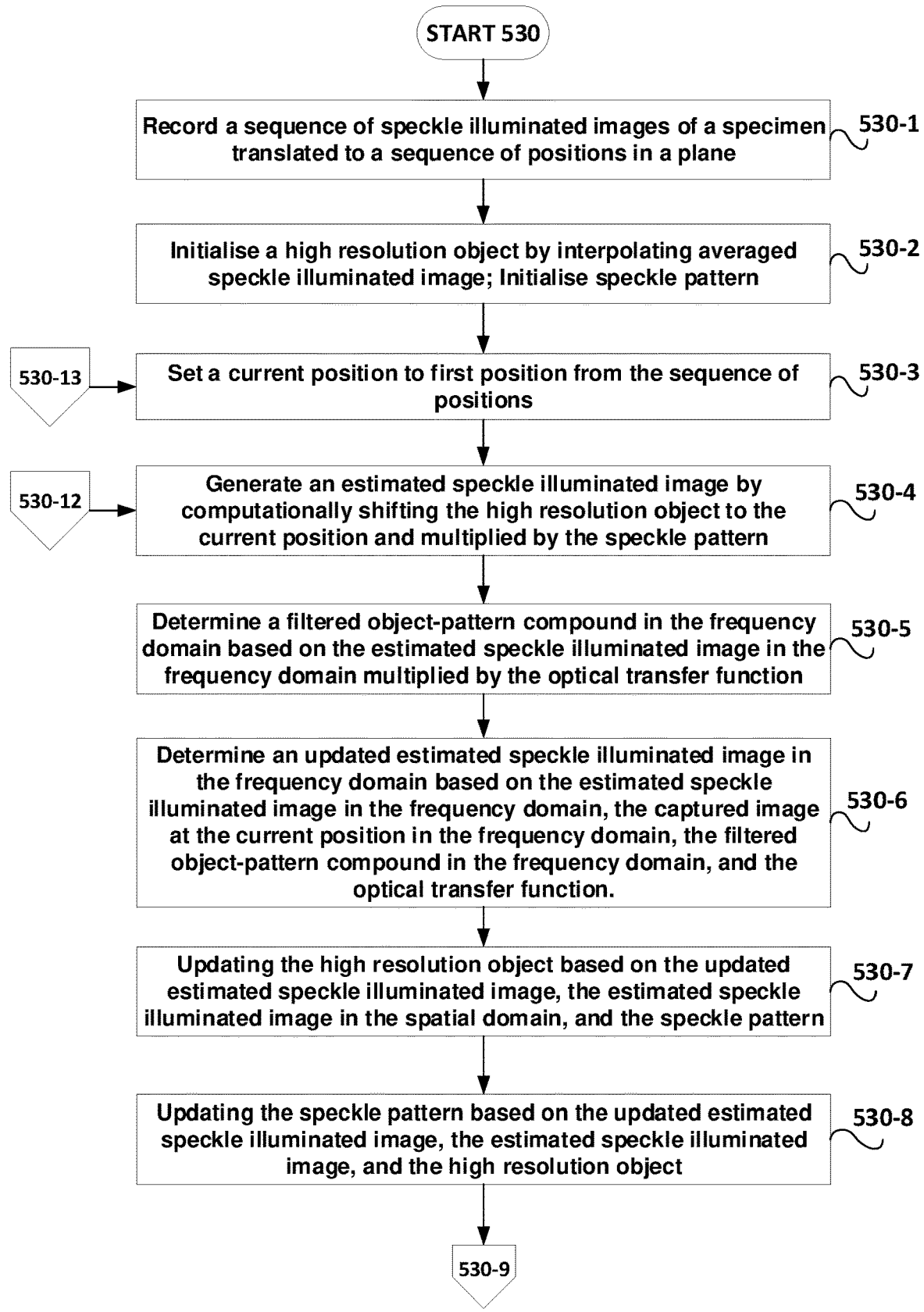
FIGS. 5B and 5C is a flowchart representing an example computer-implemented method of reconstructing a UV-AutoM image through a sequence of speckle-illuminated low-resolution images.
Figure 5C:
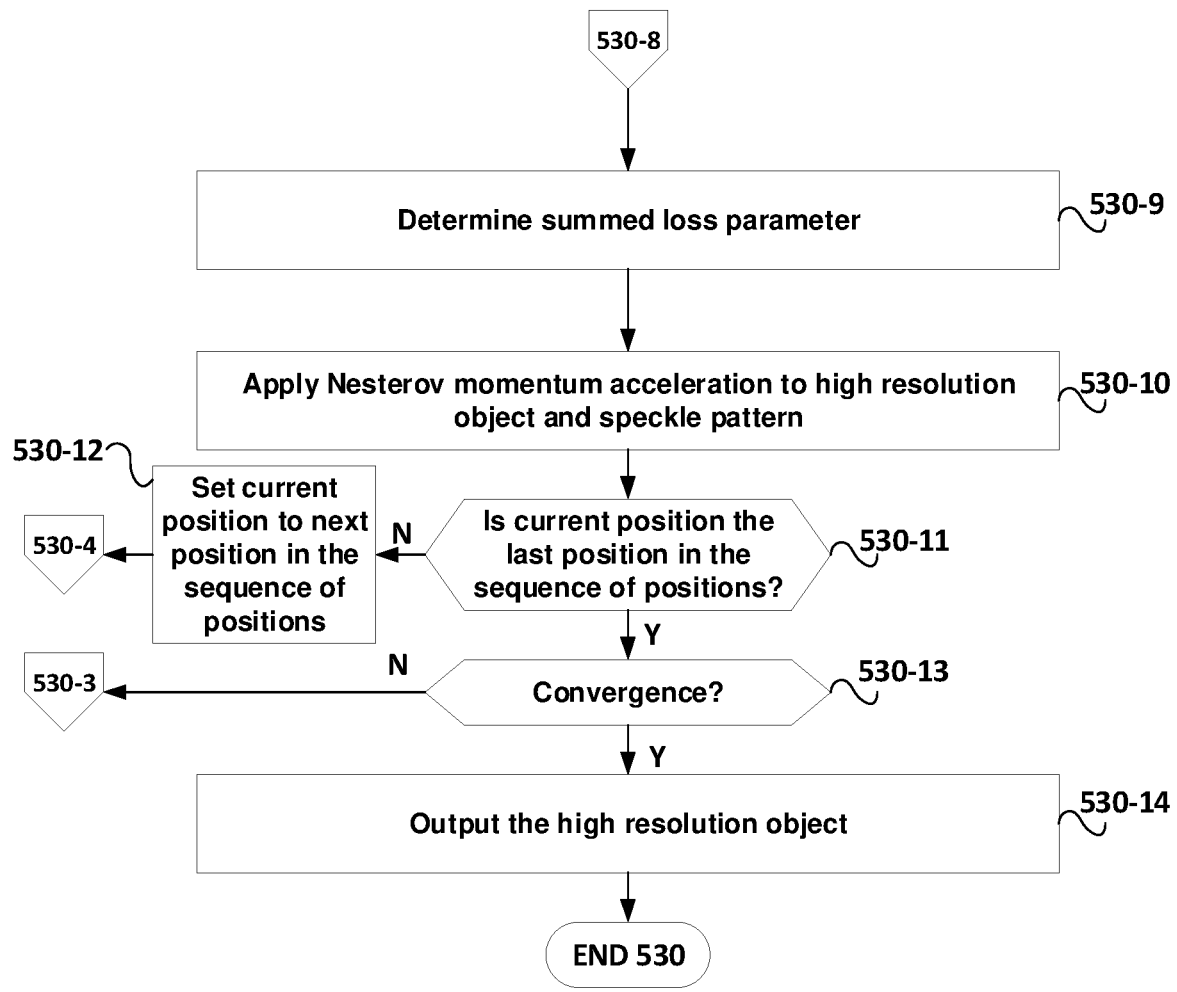

Referring to FIGS. 5B and 5C there is shown flowchart representing an example computer-implemented method 530 of reconstructing a UV-excited autofluorescence image (UV-AutoM) from a sequence of speckle-illuminated images. The computer-implemented method 530 can be performed by a computer system 100 as described in relation to FIGS. 1A and 1B or by an embedded device 201 as described in relation to FIGS. 2A and 2B. FIG. 5D provides pseudocode further representing a more specific implementation of reconstructing a high-throughput UV-excited autofluorescence image (UV-AutoM) from a sequence of speckle-illuminated images. The flowchart of FIGS. 5B and 5C will be described herein with reference to the pseudocode of FIG. 5D.

In particular, at step 530-1, the method 530 includes recording a sequence of speckle illuminated images $I_j$ (j=1,2, . . . , N) of a specimen translated to a respective sequence of positions in a plane along a scanning trajectory. The sequence of speckle illuminated images I are low resolution images in the sense that the output of method 530 is a high resolution image which has a higher resolution compared to each of the low resolution speckle illuminated images $I_j$. In one example, the sequence of speckle illuminated images could be captured using a 4×/0.1NA objective lens.

At step 530-2, the method 530 includes initializing an image object o(x,y), herein referred to as a high resolution image object, and a speckle pattern. As shown in line 3 of the pseudocode, the sequence of speckle illuminated images are averaged and the averaged speckle illuminated image is interpolated, wherein the high resolution image object o(x,y) is set to the result of the interpolation of the averaged speckle illuminated image. The speckle pattern is initialized to a matrix of ones.

At step 530-3, a current position is set to a first position from the sequence of positions. The current position in the pseudocode of FIG. 5D is represented by ($x_j,y_j$).

Steps 530-4 to 530-11 are performed for each speckle-illuminated image in the captured sequence in the form of an inner loop of the flowchart illustrated in FIGS. 5B and 5C. Referring to the pseudocode of FIG. 5D, the inner loop represents lines 6 to 14, and an outer loop is represented by lines 5 to 17. For the inner loop, effectively the current position variable is incremented to the next position in the sequence of positions and the corresponding speckle illuminated image at the respective current position is used in image processing steps to modify the high resolution image object and the speckle pattern.

More specifically, at step 530-4 the method 530 includes generating an estimated speckle illuminated image $\varphi_j(x,y)$ by computationally shifting the high resolution object to the current position o($x-x_j,y-y_j$) which is then multiplied by the speckle pattern p(x,y). This is shown in line 7 of the pseudocode of FIG. 5D.

At step 530-5, the method 530 includes determining a filtered object-pattern compound, $\psi_j(k_x,k_y)$, in the frequency domain based on the estimated speckle illuminated image in the frequency domain, $F(\varphi_j(x,y))$, which is multiplied with an optical transfer function, $OTF(k_x, k_y)$ where kx and ky are spatial coordinates in the frequency domain. The optical transfer function is the known optical transfer function of the apparatus used for capturing the sequence of speckle illuminated images of the specimen.

It is noted that the shifting operation in steps 530-4 and 530-5 are collectively an application of angular spectrum.

Steps 530-6 to 530-8 described below are reconstruction procedures based on a phase retrieval algorithm termed Ptychographic iterative engine (PIE).

At step 530-6, the method 530 includes determining an updated estimated speckle illuminated image in the frequency domain, $F(\varphi_j^{update})$, based on the estimated speckle illuminated image in the frequency domain, the captured speckle illuminated image at the current position in the frequency domain, the filtered object-pattern compound in the frequency domain, the optical transfer function, and an adaptive learning rate parameter a. More specifically, line 9 of the pseudocode of the FIG. 5D shows the specific calculation for the updated estimated speckle illuminated image in the frequency domain which is shown by Equation 1 below:

$$F(\varphi_j^{update}) = F(\varphi_j) + \alpha * \text{conj}(OTF) * [F(I_j) - \psi_j] / |OTF|_{max}^2 \quad \text{Equation 1}$$

In particular, the updated estimated speckle illuminated image in the frequency domain is calculated to equal the estimated speckle illuminated image in the frequency domain summed with to the adaptive learning rate parameter multiplied by a conjugate of the optical transfer function multiplied by a difference between the captured speckle illuminated image at the current position in the frequency domain and the filtered object-pattern compound in the frequency domain divided by the square of the absolute maximum value of the optical transfer function.

At step 530-7, the method 530 includes updating the high resolution object based on the updated estimated speckle illuminated image in the spatial domain, and the speckle pattern. This is shown in line 10 of the pseudocode of FIG. 5D and represented by Equation 2 below:

$$o(x-x_j, y-y_j) = o(x-x_j, y-y_j) + \text{conj}(p) * (\varphi_j^{update} - \varphi_j) / |p|_{max}^2 \quad \text{Equation 2}$$

In particular, the high resolution object is set to equal the high resolution object summed with the conjugate of the speckle pattern multiplied by the difference between the updated estimated speckle illuminated image in the spatial domain and the estimated speckle illuminated image in the spatial domain divided by the square of the absolute value of the maximum value of the speckle pattern.

At step 530-8, the method 530 includes updating the speckle pattern based on the updated estimated speckle illuminated image, the estimated speckle illuminated image, and the high resolution object. This is shown in line 11 of the pseudocode of FIG. 5D and represented by Equation 3 below:

$$p = p + \text{conj}(o) * (\varphi_j^{update} - \varphi_j) / |o|_{max}^2 \quad \text{Equation 3}$$

In particular, the speckle pattern is set to equal the speckle pattern summed with the conjugate of the high resolution object multiplied by the difference between the updated estimated speckle illuminated image in the spatial domain and the estimated speckle illuminated image in the spatial domain divided by the square of the absolute value of the maximum value of the high resolution object.

At step 530-9, a summed loss parameter, loss; is calculated for the current loop based on the absolute value of the difference between the captured speckle illuminated image $I_j$ and the inverse Fourier transformation of the filtered object-pattern compound in the frequency domain $\psi_j$. This is shown in line 12 of the pseudocode of FIG. 5D and represented by Equation 4 below:

$$\text{loss}_j = \Sigma_j |I_j - F^{-1}(\psi_j)| \quad \text{Equation 4}$$

At step 530-10, the method 530 includes applying Nesterov momentum acceleration to the high resolution object and the speckle pattern. This is performed to accelerate gradient decent of the reconstruction process for faster convergence.

At step 530-11, the method 530 includes determining if the current position is the last position in the sequence of positions. In response to a positive determination (i.e. 'yes'), the method proceeds to step 530-13. In response to a negative determination (i.e. 'no'), the method then proceeds to step 530-12.

At step 530-12, the method 530 includes setting the current position to the next position in the sequence of positions. The method 530 then proceeds to back to step 530-4 to perform one or more further iterations of the inner loop represented by steps 530-4 to 530-11 until the last speckle illuminated image has been processed.

At step 530-13, the method 530 includes determining if convergence has been detected based on the summed loss parameter. This is determined by determining a loss ratio calculated based on a difference between the summed loss parameter calculated for the previous and current iteration of the inner loop (i.e. steps 530-4 to 530-11) divided by the summed loss parameter for the previous iteration of the inner loop. The loss ratio is then compared to a loss threshold, which in the example pseudocode of FIG. 5D is set to 0.01. If the loss ratio is less than or equal to the loss threshold, the adaptive learning rate parameter a is reduced, in this example the adaptive learning rate parameter a is halved. The adaptive learning rate parameter a is adjusted to suppress oscillation of the loss function near the converging point to minimize the artifacts in the reconstructed image. The reconstruction process will end once the learning rate a is reduced to zero, such that a high-resolution object has been determined and output at the step 530-14. The high resolution image object that is output is a high-resolution UV-AutoM image with enhanced subcellular resolution across centimeter-scale imaging area which has increased resolution compared to each speckle illuminated low resolution image provided as input to the reconstruction method 530. The speckle pattern which was initially unknown at the start of method 530 is also determined at step 530-14.

This computational imaging method represented by method 530 synthesizes a sequence of speckle-illuminated low-resolution images to reconstruct a high-resolution autofluorescence image (UV-AutoM). The method is achieved through a series of updating processes in the spatial domain and the frequency domain. The method begins with an initial guess of the high-resolution object. The object is firstly multiplied with the speckle pattern, Fourier transformed to frequency domain and low-pass filtered by the optical transfer function. Then the filtered spectrum is inverse transformed to the spatial domain with intensity replaced by the corresponding speckle-illuminated low-resolution image. Finally this updated autofluorescence image is transformed to the frequency domain and further updated. One iteration is completed until all the captured low-resolution images are involved, and Nesterov momentum acceleration is implemented for faster gradient descent. A high-resolution UV-AutoM image is output after several iterations, with enhanced subcellular resolution across centimetre-scale image area. The prior knowledge of the speckle pattern is not required, only the relative shift between each low-resolution image should be known.

A high-resolution UV-AutoM image will be output after several iterations, with enhanced subcellular resolution across centimeter-scale image area. The prior knowledge of the speckle pattern is not required, only the relative shift ($x_j$, $y_j$) between each captured image should be known. There suggests that sufficient scanning range (larger than ~2 low-NA diffraction-limited spot size) and finer scanning steps (smaller than the targeted resolution) can reduce distortions in the reconstruction, and the final achievable NA is the sum of objective's NA and speckle NA.

Figure 6:
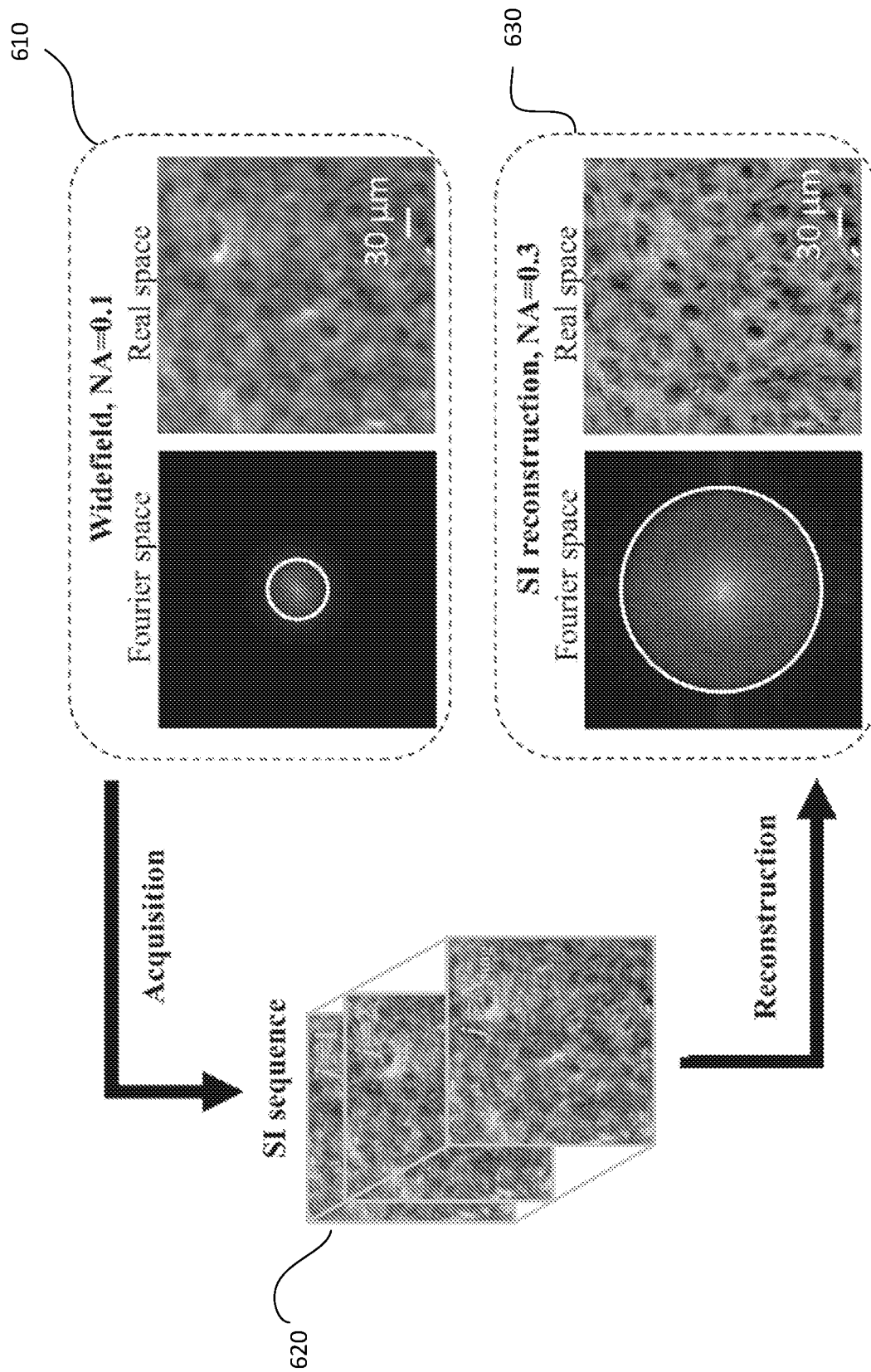
FIG. 6 shows a graphical representation of an example of an SI reconstruction method and system for reconstructing a UV-AutoM image.

FIG. 6 shows a graphical representation of an example of an SI reconstruction method and system described previously in relation to FIGS. 5A to 5C. FIG. 6 shows at 610 physical constraint set by a 4×/0.1NA objective in the Fourier space and the corresponding low resolution raw image of a mouse brain sample (100-μm thickness). An SI dataset 620 is acquired using the 4×/0.1NA objective as shown in FIG. 6 which in this example comprises of 49 speckle-illuminated low-resolution measurements, captured by translating the sample to 49 different positions in X-Y plane with 500-nm scanning step size. The SI dataset can then be used to reconstruct a high-throughput UV-AutoM image 630 with an extended passband up to NA=0.3, which corresponds to 3 times resolution enhancement compared with the images acquired using the 4×/0.1NA objective.

Figure 7A:
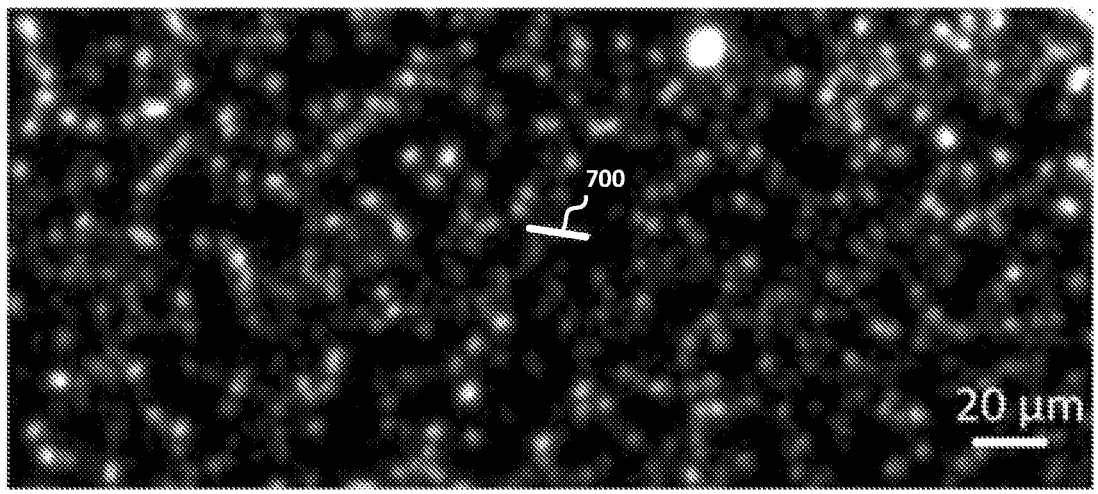
FIG. 7A is an example of a low-resolution UV-AutoM image captured by a 4λ/0.1 NA objective.
Figure 7B:
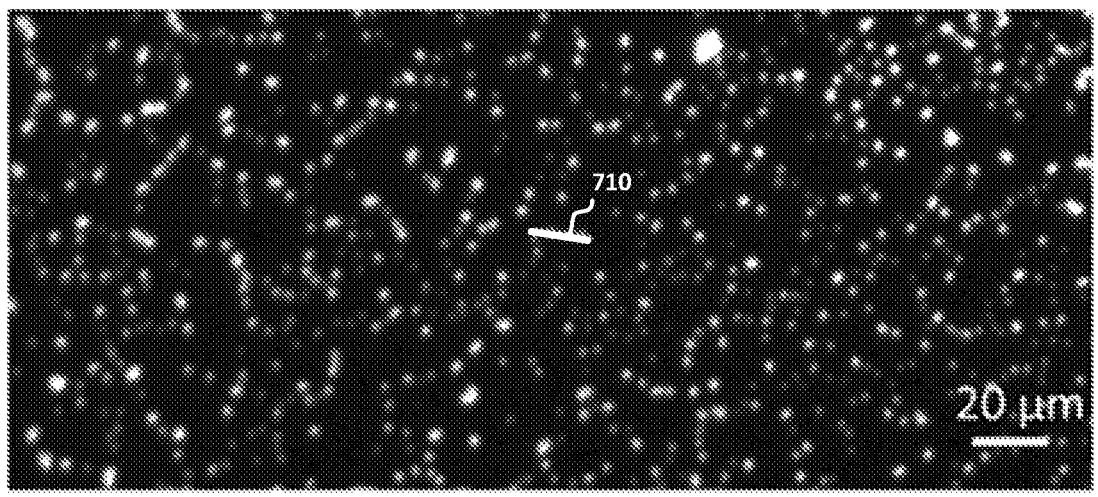
FIG. 7B is an example of a high-resolution UV-AutoM image reconstructed by the method of FIGS. 5B and 5C.
Figure 7C:
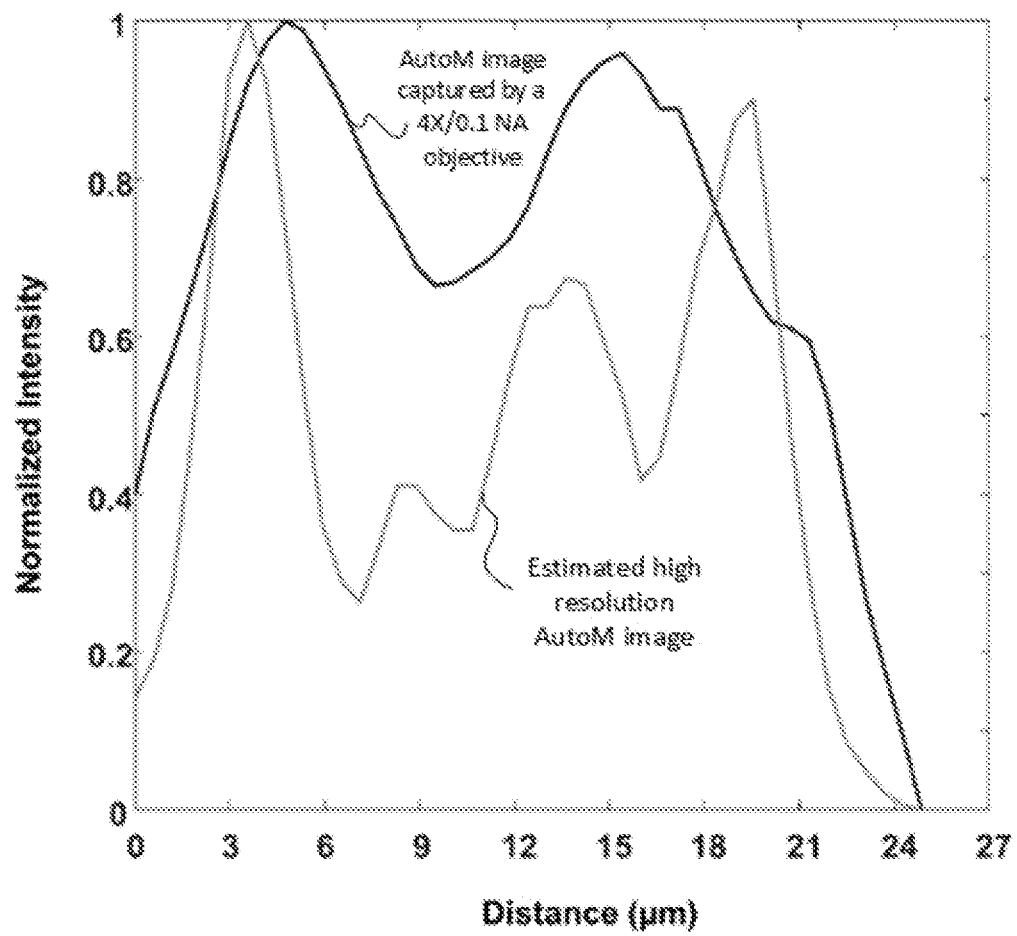
FIG. 7C is a line profile of the lines 700 and 710 marked in FIGS. 7A and 7B, respectively.

Fluorescence nanoparticles with a diameter of 500 nm (excitation/emission: 365 nm/445 nm, B500, available from Thermo Fisher) can be used to quantify resolution performance of the SI reconstruction method and system described above. Referring to FIG. 7A there is shown an example of a low-resolution fluorescence image captured with a 4×/0.1NA objective under uniform illumination, while FIG. 7B is a reconstructed high resolution fluorescence image through 49 speckle-illuminated low-resolution images that raster scanned with a step size of 500 nm. Both FIGS. 7A and 7B are captured using a 266-nm UV laser. FIG. 7C is an intensity plot along the solid lines 700, 710 indicated in FIGS. 7A and 7B, from which we can quantify the resolution enhancement by the disclosed SI reconstruction method and system.

Figure 8A:
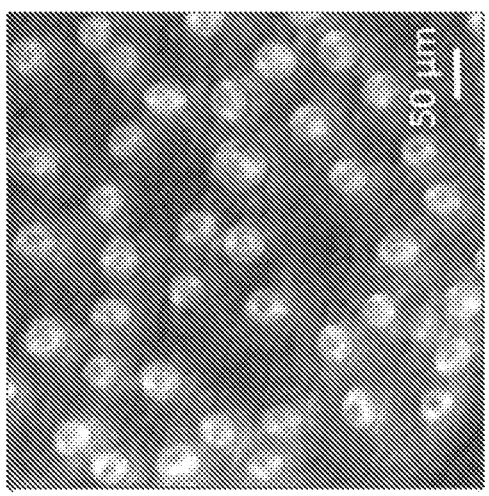
FIGS. 8A and 8B show examples of UV-AutoM images of two leaf samples with rough surface captured by a 4×/0.1 NA objective.
Figure 8B:
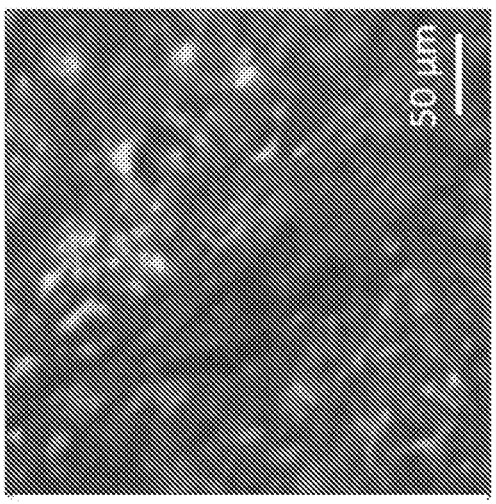
Figure 8C:
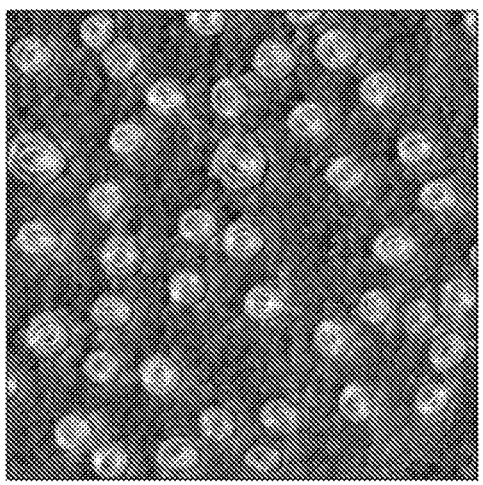
FIGS. 8C and 8D show examples of high-resolution UV-AutoM images reconstructed from a plurality of speckle-illuminated low-resolution images using the method of FIGS. 5B and 5C.
Figure 8D:
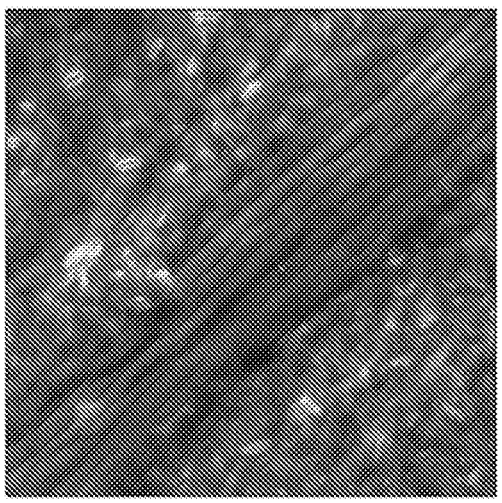
Figure 8E:
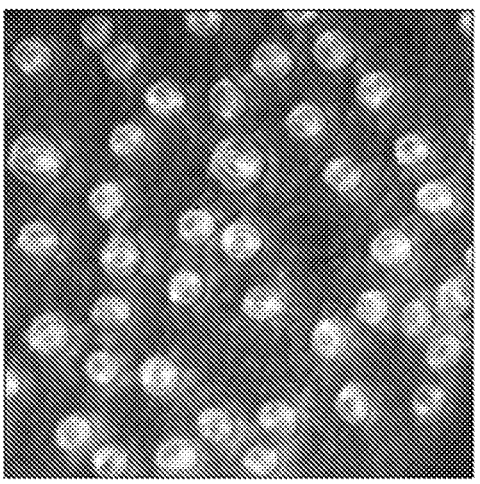
FIGS. 8E and 8F show a high-resolution reference image of the two leaf samples of captured in FIGS. 8A and 8B using a 10λ/0.3NA objective.
Figure 8F:
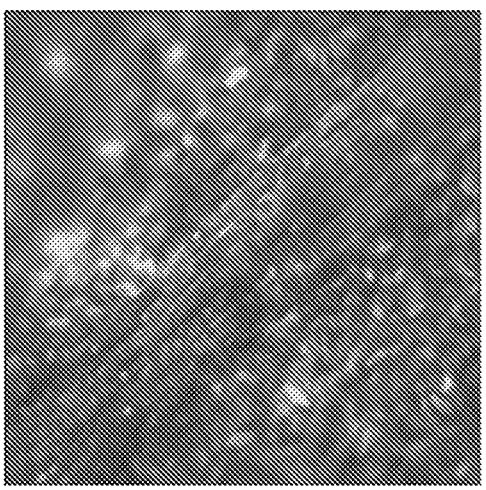

Advantageously, the SI reconstruction method and system can be highly tolerant to a rough surface. To demonstrate high tolerance to rough surface of our system, FIGS. 8A-8C shows UV-AutoM images of two unprocessed leaf samples. FIGS. 8A and 8B shows low resolution autofluorescence images captured with a 4×/0.1NA objective, while FIGS. 8C and 8D shows high resolution SI reconstructed UV-AutoM images through 49 speckle-illuminated low-resolution images scanned with a step size of 500 nm. FIGS. 8E and 8F show the corresponding high resolution reference images captured with a 10×/0.3NA objective, presenting obvious out-of-focus regions compared with FIGS. 8C and 8D due to the shallow DOF of high-NA objective, demonstrating that the high resolution UV-AutoM image reconstructed by SI method via a low-NA objective can far outperform high-NA objective especially when dealing with a rough surface.

Figure 9A:
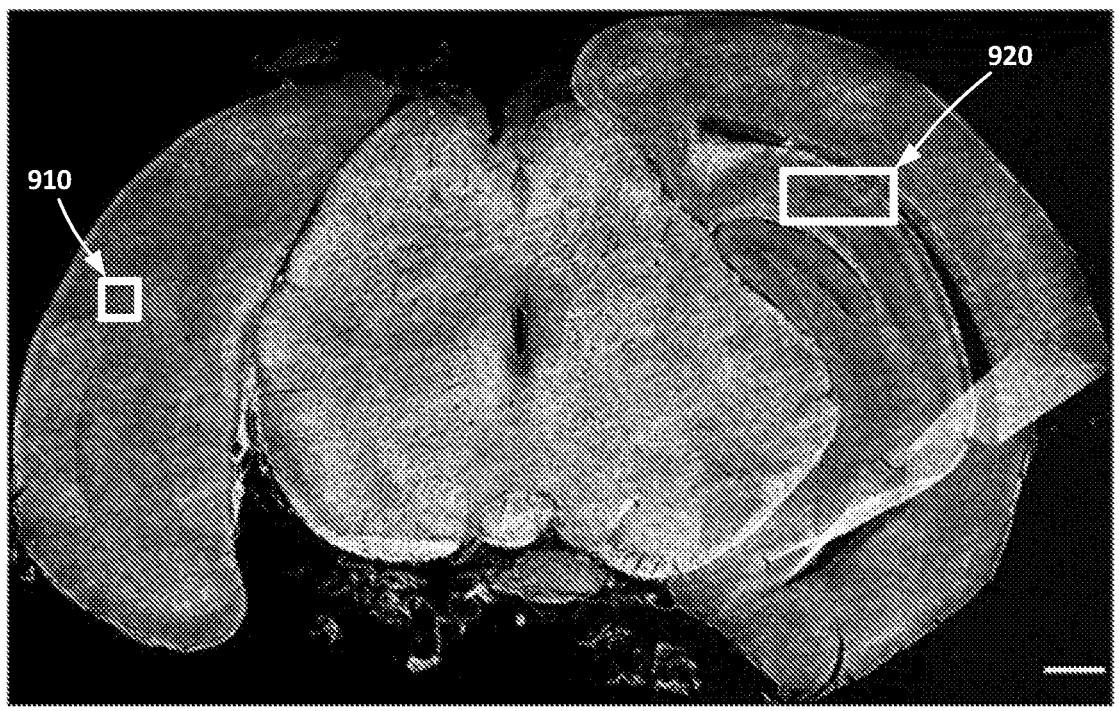
FIG. 9A is a UV-AutoM image of the whole mouse brain (FFPE section after deparaffinization, 4-µm thickness) with a scale bar of 500 µm.
Figure 9B:
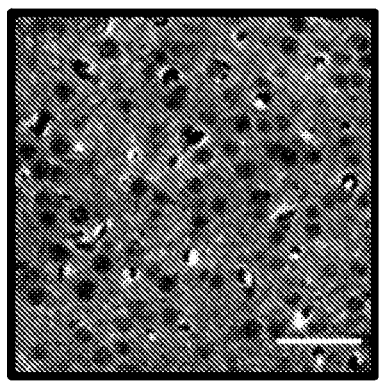
FIGS. 9B and 9C are magnified views of boxes 910 and 920 in FIG. 9A, each with a scale bar of 50 µm.
Figure 9C:
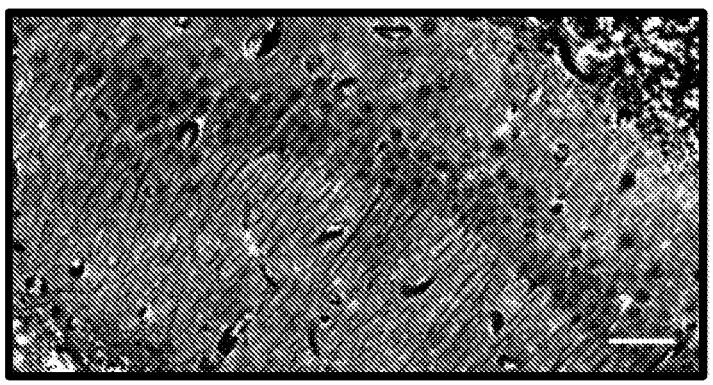
Figure 9D:
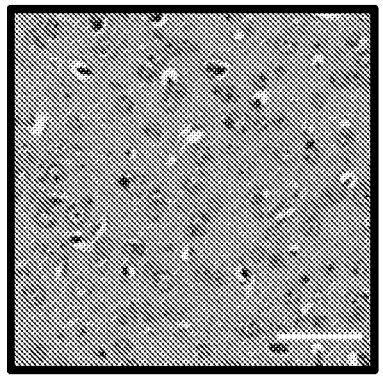
FIGS. 9D and 9E are bright-field H&E-stained images corresponding to FIGS. 9B and 9C, each with a scale bar of 50 µm.
Figure 9E:
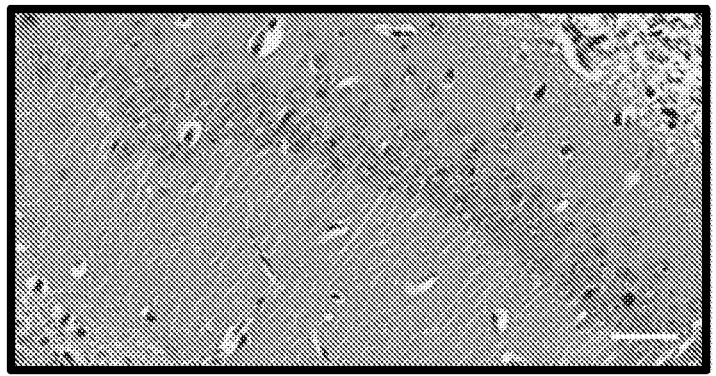

Referring to FIGS. 9A to 9F, there is shown structural matching between UV-AutoM and bright-field H&E-stained images. FIG. 9A is a UV-AutoM image of the whole mouse brain slide (FFPE section after deparaffinization, 4-μm thickness), FIGS. 9B and 9C are zoomed-in images of boxes 910 and 920 in FIG. 9A respectively, while FIGS. 9D and 9E are respectively the corresponding bright-field H&E histological images captured by a digital slide scanner (NanoZoomer SQ, Hamamatsu). It can be seen that the cells concentrated at margin (box 910) and hippocampus (box 920) areas are clearly resolved in the UV-AutoM images with negative contrast, i.e. appear black on images, and demonstrate substantially perfect structural matching (both cell morphology and distribution) with the H&E-stained images.

Figures 10D, 10E, 10F, 10G, 10H:
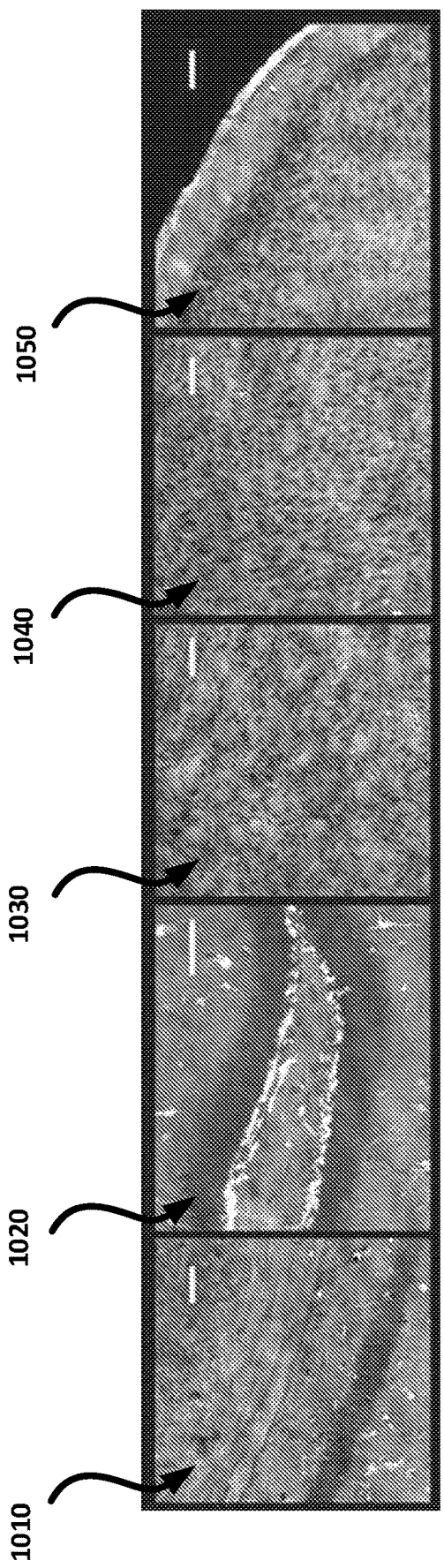
FIGS. 10D to 10H show high-throughput sub-views of five functional regions of the mouse brain as depicted in the reconstructed UV-AutoM image of FIG. 10C.

Referring to FIG. 10A to 10G there is shown a high-throughput label-free visualization of a thick mouse brain (100-μm thickness, cut by a Leica vibratome). Due to the shallow penetration depth of UV light, the excited autofluorescence is superficially localized within a few microns below the surface, thus allowing label-free and slide-free imaging of thick specimen. Furthermore, application of the SI reconstruction method and system disclosed above to achieve rapid high-resolution visualization of the whole mouse brain via a 4× objective lens, results in less imaging aberrations and allows higher tolerance to rough tissue surface compared with 10× objective lens. FIG. 10A shows an example image of a top view of a mouse brain. FIGS. 10B and 10C are examples of reconstructed UV-AutoM images each depicting a cross-sectional cut through respective positions (lines A-A and B-B) of the mouse brain of FIG. 10A wherein each reconstructed UV-AutoM image is generated using an SI dataset comprising of 441 speckle-illuminated low-resolution images. The exposure time was 200 ms for each low resolution raw image, enabling fast imaging with a total acquisition time within 3 minutes. FIGS. 10D to 10H show high-throughput sub-views of five functional regions in FIG. 10C, including (a) corpus callosum 1010, (b) hippocampus 1020, (c) globus pallidus 1030, (d) caudoputamen 1040, and (e) parietal cortex 1050.

Generation of Pseudo-Stained Histological Images

Pathologists are typically trained for examining histologically-stained tissue samples to make diagnostic decisions. However, both UV-PAM and UV AutoM images are grayscale images. To address or alleviate this issue, a deep-learning based virtual staining method, utilising a generative adversarial network (GAN), is disclosed for transforming a UV-PAM or UV-AutoM image of an unlabeled tissue into a pseudo-hematoxylin and eosin (H&E) stained image.

The GAN allows virtual staining of unpaired UV-PAM/ UV-AutoM and H&E images, thereby largely simplifying the image pre-processing procedure, which is difficult as tissue may be rotated or deformed during the staining process. A paired training method can also be employed with the UV-PAM/UV-AutoM images with the corresponding H&E-stained images in order to perform pseudo-coloring.

In certain embodiments, the UV-PAM image generated using the method and system described in relation to FIG. 3 and the SI reconstruction UV-AutoM images generated using the system and method of FIGS. 5A, 5B and 5C can be provided as input to the trained cycle-GAN in order to generate pseudo-stained histological images. Additionally or alternatively, UV-PAM images generated using the system and method disclosed in US Patent Application No. 2014/ 0356897, the contents of which is herein incorporated by reference in its entirety, can be used as input to the GAN to generate the pseudo-stained histological images.

Figure 11A:
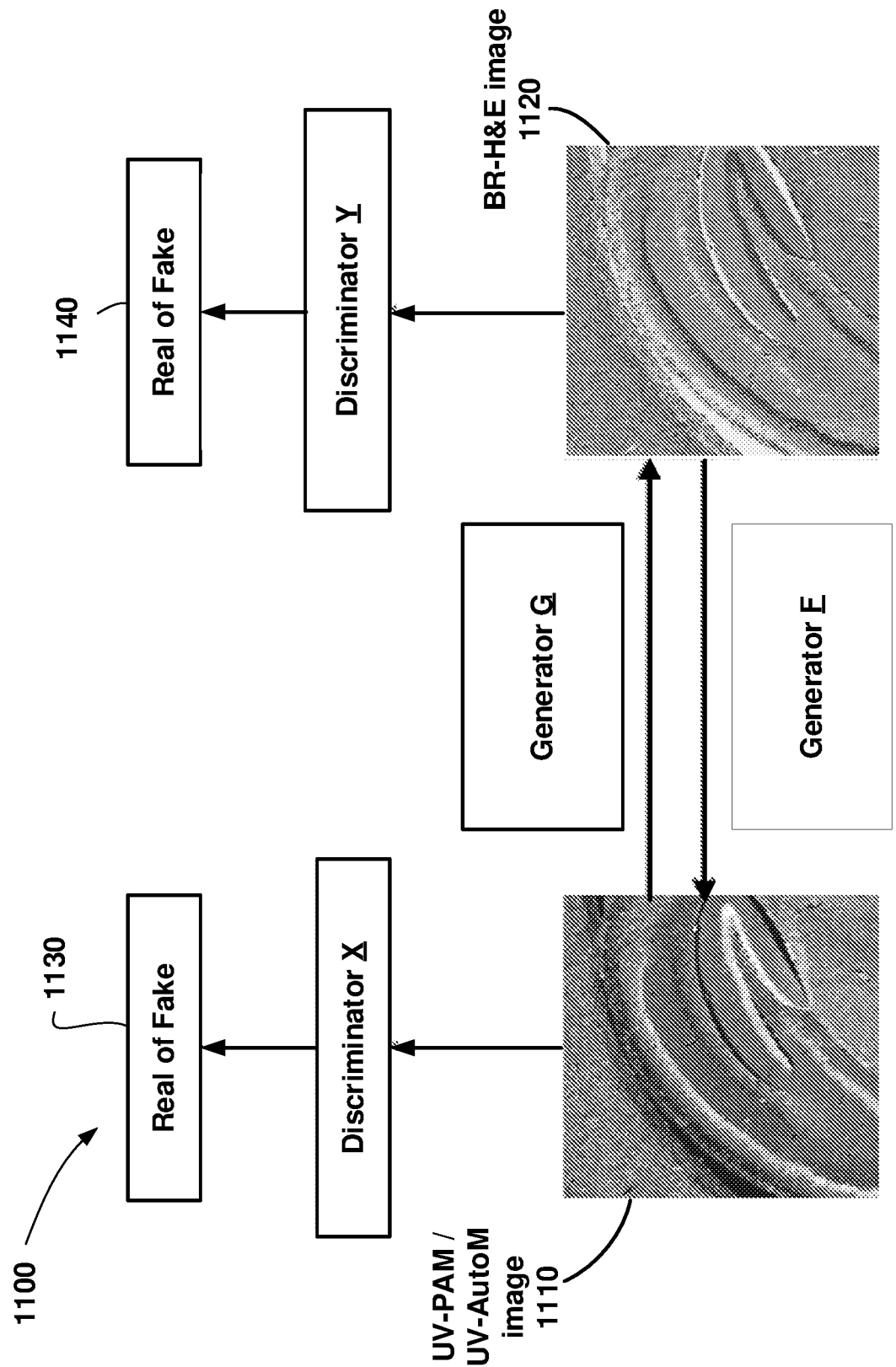
FIG. 11A is a functional block diagram representing an example computer implemented system for generating a pseudo-stained histological image (i.e. virtual stained histological image).

Referring to FIG. 11A there is shown a block diagram representing an example computer implemented system for generating a pseudo-stained histological image (i.e. virtual stained histological image). The computer implemented system can be implemented using computer system 100 or embedded system 201.

The computer implemented system utilizes a generative adversarial network 1100 (GAN) which can be provided in the form of a cycle-consistent generative adversarial network (Cycle-GAN). The cycle-GAN 1100 comprises of four deep convolutional neural networks, namely a first generator module G, a second generator module F, a first discriminator module X and a second discriminator module Y.

As shown in FIG. 11A, generator G is configured to learn to transform UV-AutoM/UV-PAM input images 1110 (exemplified as a UV-PAM image) to bright-field H&E images 1120 (exemplified as a BR-HE image) while generator F is configured to learn to transform bright-field H&E images 1120 to UV-AutoM/UV-PAM images 1110. Discriminator X is configured to distinguish between real UV-PAM images and fake UV-PAM images produced by generator F, as shown by output 1130, and at the same time, discriminator Y is configured to discriminate between real bright-field H&E images and fake bright-field H&E images produced by generator G, as shown as output 1140. Once the generator G can produce H&E images that the discriminator Y cannot distinguish from input real H&E images, the generator G has learned this transformation from UV-AutoM/UV-PAM images to H&E images. Similarly, once the generator F can produce UV-AutoM/UV-PAM images that the discriminator X cannot distinguish from real H&E images, the generator F has learned this transformation from H&E images to UV-AutoM/UV-PAM images.

Figure 11B:
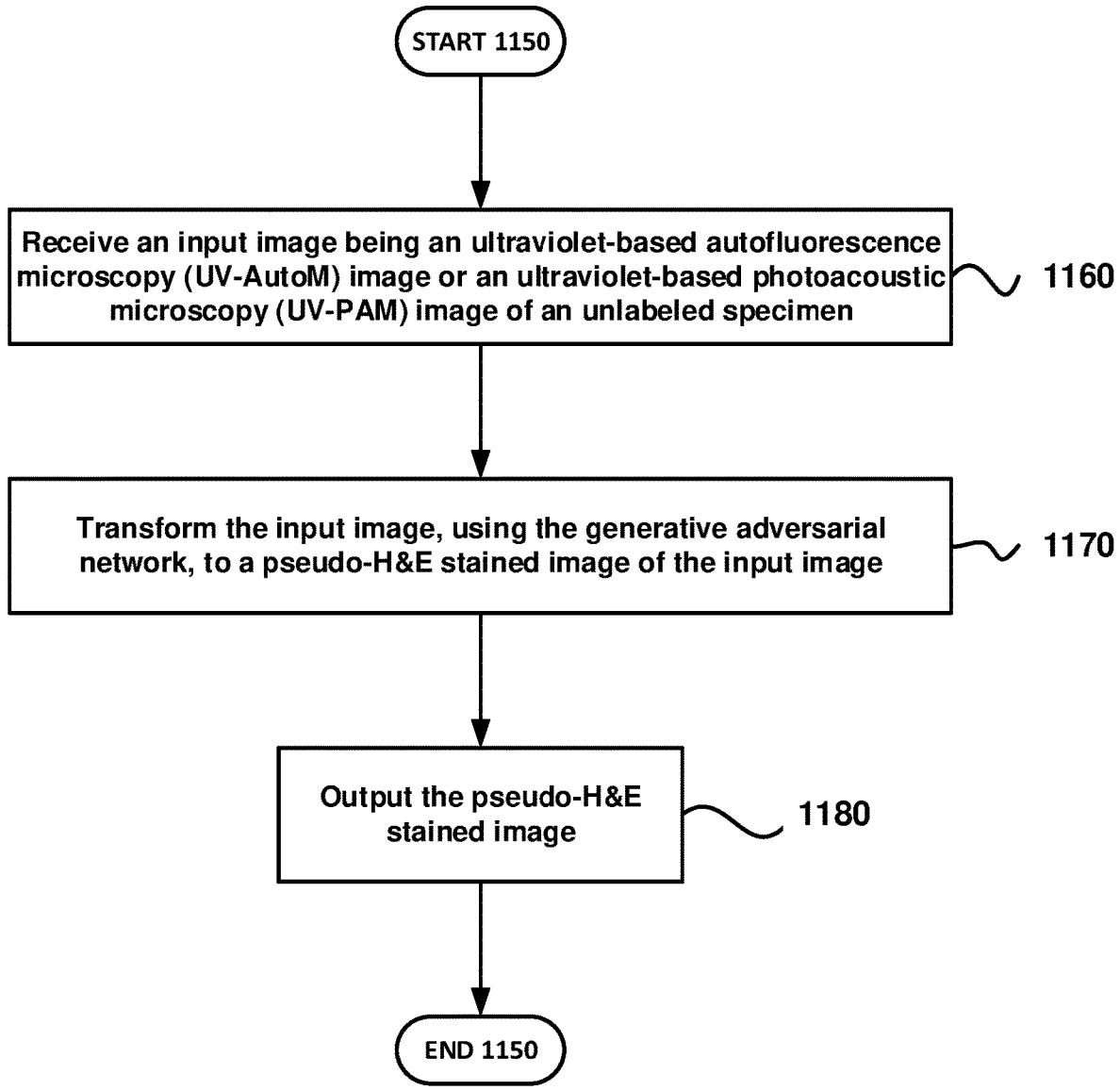
FIG. 11B is a flowchart representing an example computer implemented method 1150 for generating a pseudo-hematoxylin and eosin (H&E) stained image.

Referring to FIG. 11B there is shown a flowchart representing an example computer implemented method 1150 for generating a pseudo-hematoxylin and eosin (H&E) stained image. The computer implemented method can be performed by computer system 100 or embedded system 201.

At step 1160, the method 1150 includes receiving an input image. The input image is an ultraviolet-based autofluorescence microscopy (UV-AutoM) image or an ultraviolet-based photoacoustic microscopy (UV-PAM) image of an unlabeled specimen. The input image is a grayscale image.

At step 1170, the method 1150 includes transforming the input image, using the generative adversarial network, to a pseudo-H&E stained image of the input image.

At step 1180, the method 1150 includes outputting the pseudo-H&E stained image.

Preferably, the generative adversarial network is a generative adversarial network with cycle consistency.

In certain implementations, the method 1150 includes training the generative adversarial network using unpaired input and H&E stained images.

Figure 12:
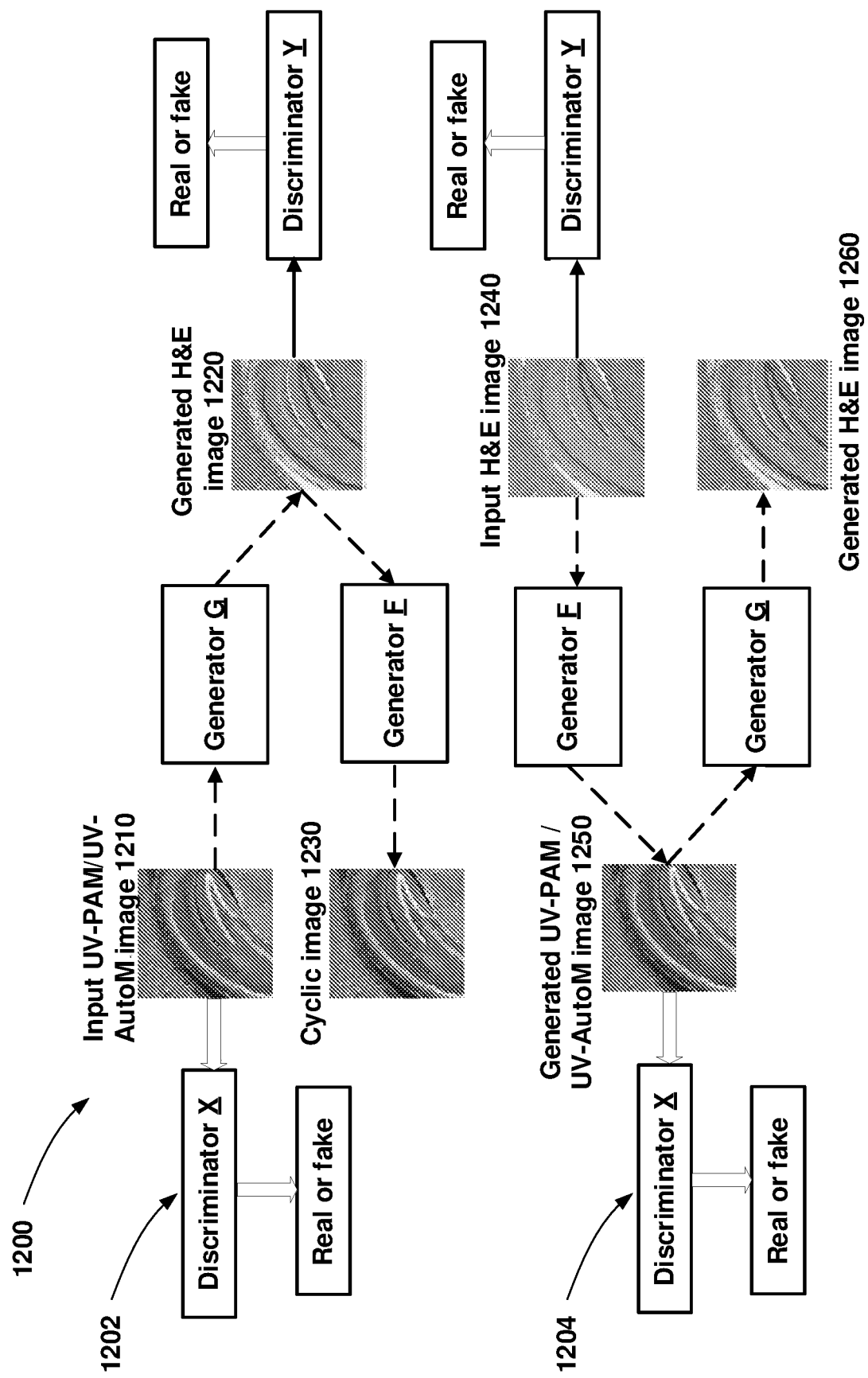
FIG. 12 is a functional block diagram representing a detailed workflow of a forward cycle and backward cycle of a Cycle-GAN.

Referring to FIG. 12 there is shown a functional block diagram representing a detailed workflow 1200 of a forward cycle 1202 and backward cycle 1204 of the cycle-GAN 1100 of FIG. 11. The cycle generative adversarial network comprises of four deep convolutional neural networks including: a first generator G configured to transform the input image to a generated H&E image; a second generator F configured to transform a H&E image to a generated UV-AutoM or UV-PAM image; a first discriminator Y configured to discriminate between a H&E image of a training set and a generated H&E image generated by the first generator deep convolutional neural network; and a second discriminator X configured to discriminate between a UV-AutoM or UV-PAM image of the training set and a generated UV-AutoM or UV-PAM image generated by the second generator deep convolutional neural network.

More specifically, the forward cycle 1202, which shown in the top row of the schematic shown in FIG. 12, after inputting one UV-AutoM/UV-PAM image 1210 (herein referred to as the input image) to generator G, wherein the generator G outputs a generated H&E image 1220. Discriminator Y is configured to determine if the generated H&E image 1220 is real or fake (i.e. the Discriminator Y is configured to identify if the H&E images received from generator G is originated from input real H&E images or from generator G). In turn, the generated H&E image 1220 of the generator G is provided as input to the generator F to be transformed back to a UV-AutoM/UV-PAM image 1230, which is referred to as the cyclic image 1230. The loss between the input image 1210 and cyclic image 1230 is referred to as cycle-consistency loss in cycle-GAN. As shown in a bottom row 1204 of the schematic of FIG. 12, the backward cycle is symmetrical to the forward cycle. The backward cycle starts from the input H&E image 1240, wherein the backward cycle learns to transform BR-H&E images 1240 to UV-AutoM/UV-PAM image images 1250. Similarly, discriminator X is configured to determine if the generated UV-AutoM/UV-PAM image is real or fake by comparing it with the input image.

Figure 13:
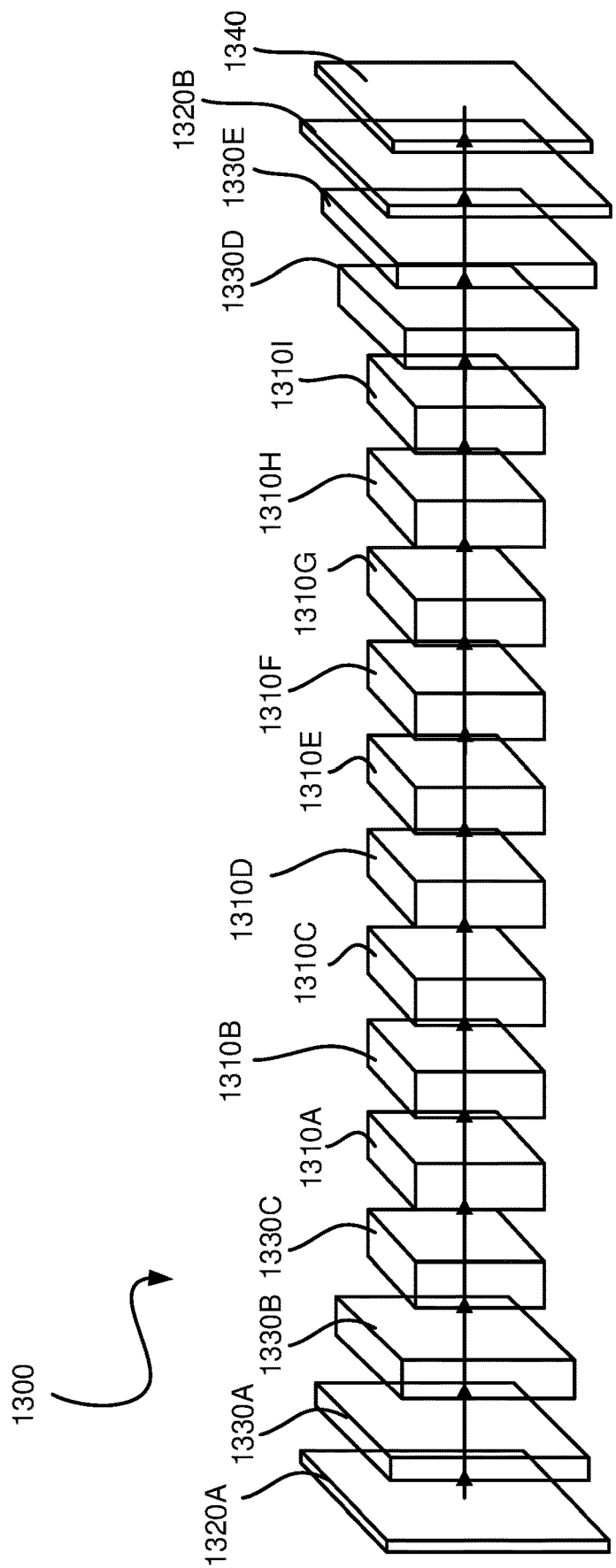
FIG. 13 is a functional block diagram representing an example generator of the Cycle-GAN of FIG. 11.

Referring to FIG. 13 which shows a functional block diagram representing an example generator 1300 of the Cycle-GAN of FIG. 11A. In one form, the first and second generator, generator G and F, can be configured as Resnet-based generator networks. In alternate embodiments, generator G and F can be configured as U-Net-based generator networks. Each Resnet-based generator can be composed of several down-sampling layers 1320A, 1330A, 1330B, 13330C, residual blocks 1310A-1310I, and up-sampling layers 1330D, 1330E and 1320B. In the example shown in FIG. 13, 9 residual blocks 1310A-1310I are to train the UV-PAM and HE images, each with a pixel number of 256×256. Spatial reflection padding (3×3) is added in the beginning of the neural networks to ensure that the input and output of the respective generator neural network have the same size. Followed by the padding layer 1320A, each Resnet based generator 1300 includes a down-sampling pathway which includes three Convolution-InstanceNorm-ReLU layers 1330A, 1330B and 1330C. In particular, the first Convolution-InstanceNorm-ReLU down-sampling layer 1330A has a larger receptive field with a kernel size 7×7 while the other two layers 1330B, 1330C have a smaller receptive field with the kernel size 3×3. The image size is recovered to the original image size and the channel is increased to 64 after the first layer 1330A. The image size is downgraded by a factor of 2 while the channel number is increased by 2 times when it passes the other two layers 1330B, 1330C. Followed by the downsampling layers 1320A, 1330A, 1330B, 1330C, it is a long residual neural network including 9 residual blocks 1310A-1310I. The image size and channel number remains unchanged (256× 64×64) when it passes each residual block. After the 9 residual blocks 1310A-1310I, the generator 1300 includes an up-sampling pathway including two Convolution-InstanceNorm-ReLU layers 1330D, 1330E with kernel size 3×3 and a reflection padding layer 1320B (3×3) coupled with Convolution-InstanceNorm-ReLU layer 1340 with kernel size 7×7. The image size is increased by a factor of 2 while the channel number is decreased by half after each up-sampling layer. After two up-sampling layers, the image size is recovered to the original image size and the channel number is decreased to 64. The last coupled layer 1340 is configured to keep the image size unchanged while decreasing the channel number to 3.

In a specific configuration, the discriminator networks Dx and Dy can be provided by 70×70 PatchGAN discriminators, which include four 4×4 Convolution-InstanceNorm-LeakyReLU layers. The PatchGAN will produce a 1-dimensional output (real or fake) after the last layer.

The described GAN was implemented using Python version 3.7.3, with Pytorch version 1.0.1. The software was implemented on a desktop computer with a Core i7-8700K CPU at 3.7 GHz and 32 GB of RAM, running an Ubuntu 18.04.2 LTS operation system. The training and testing of the Cycle-GAN neural networks were performed using a GeForce GTX 1080Ti GPUs with 11 GB RAM. However, it will be appreciated that other computer systems or embedded systems 201 can be utilized.

Examples of virtual stained histological images generated using the above described Cycle-GAN will herein be discussed.

Figure 14C:
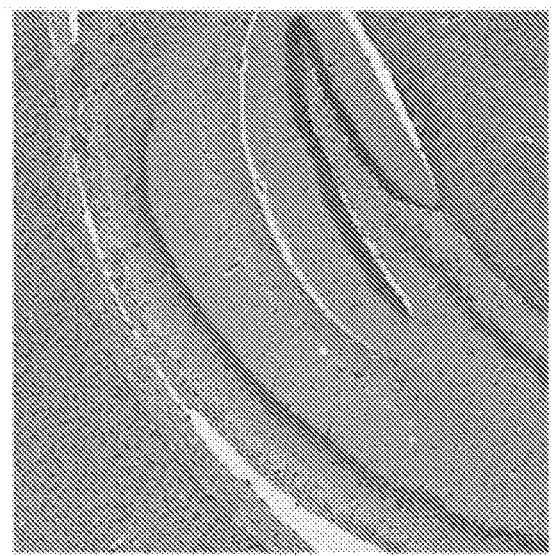
FIG. 14C is an example of a histological image of the same specimen imaged in FIG. 14A which was obtained using bright-field microscopy after H&E staining.
Figure 14B:
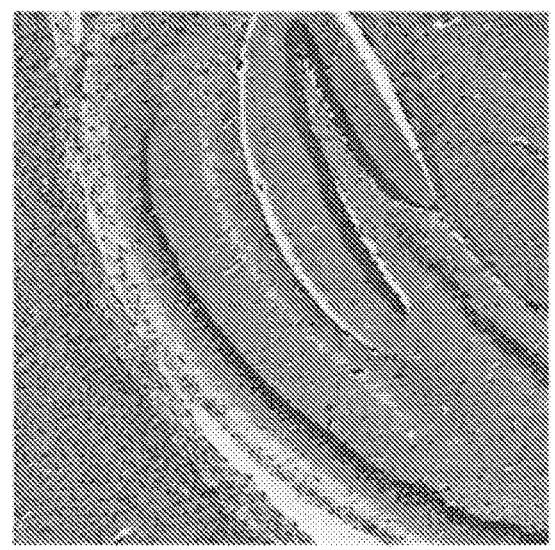
FIG. 14B is an example of a virtually-stained histological image generated as an output image by the Cycle-GAN using the grayscale UV-PAM image as the input image.
Figure 14A:
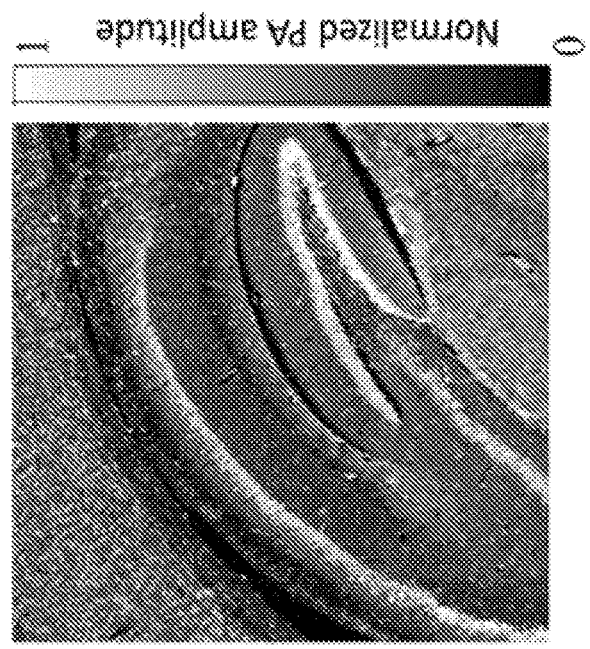
FIG. 14A is an example of a grayscale UV-PAM image of a mouse brain slice generated using the system of FIG. 3 which is provided as input to a trained Cycle-GAN configured according to FIGS. 11 to 13.

Referring to FIGS. 14A to 14C, a virtually-stained image of a UV-PAM image of a mouse brain slices were generated using the above described UV-PAM method and system and transformed using the above-described Cycle-GAN 1100. The UV-PAM image and virtually-stained image of the UV-PAM image were compared with histological images of the same sample after H&E staining. In particular, a section of specimen was imaged, which was 7 μm in thickness and was cut from a FFPE mouse brain, wherein the disclosed UV-PAM method and system was operated using raster scanning with a step size of 0.63 μm. As the UV-PAM method and system is configured to generate grayscale images, the grayscale UV-PAM image, as shown in FIG. 14A is then transformed to virtually-stained image, as shown in FIG. 14B, using the Cycle-GAN 1100 described in relation to FIGS. 11 to 13. To evaluate whether the generated virtually-stained image can provide similar information as the conventional histological image, a histological image of the same specimen was obtained using bright-field microscopy after H&E staining, as illustrated in FIG. 14C. On inspection of the color of the cell nuclei and other connective tissues on the virtually-stained image generated by the UV-PAM system, it was determined that the virtually-stained image generated by the UV-PAM system was substantially similar to the conventional histological image. Overall, the UV-PAM system combined with the deep learning system provided in the form of the disclosed Cycle-GAN 1100 generates substantially accurate virtually stained histological images without requiring conventional staining techniques.

FIGS. 15A to 15C shows an example of virtual staining of UV-AutoM images utilizing a paired training method. FIG. 15A is a UV-AutoM image of a deparaffinized FFPE mouse brain section with 7-μm thickness, and FIG. 15B is a virtual stained version of the UV-AutoM image utilizing a GAN model in the form of a paired pix2pix based network while FIG. 15C is the corresponding bright-field H&E image which served for comparison purposes. Color transformation via paired dataset enabled accurate and reliable generation of a histology-like image. However, any paired training approach requires rigorous data pre-processing procedures on image alignment and registration, and it is difficult to apply on virtual staining of thick samples. Cycle-GAN based networks were found to allow color mapping without paired training examples, and demonstrated great potential on biological tissues with any thickness. The Cycle-GAN network 1100 can be fed with unpaired UV-AutoM and H&E images from a deparaffinized FFPE mouse brain section. The well-trained Cycle-GAN 1100 network enables transformation of a UV-AutoM image of an unlabeled tissue into a virtual H&E-stained version of the unlabeled tissue, thereby allowing easy interpretation of UV-AutoM images for pathologists.

Figure 16A:
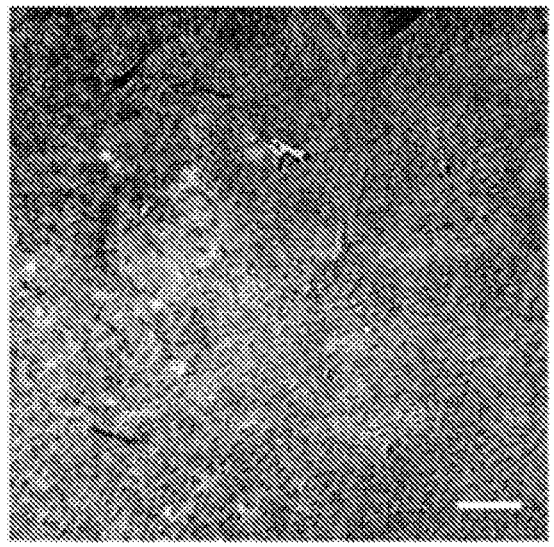
FIGS. 16A and 16B are SI reconstructed high-resolution UV-AutoM images, generated with the method of FIGS. 5B and 5C, showing mouse brain samples with a thickness of 100 µm and 200 µm, respectively.
Figure 16B:
Figure 16C:
FIGS. 16C and 16D are examples of virtually-stained H&E images generated using the computer implemented method and system of FIGS. 11 to 13.
Figure 16D:

FIGS. 16A and 16B relate to testing results of the trained Cycle-GAN network 1100 on mouse brain samples with different thicknesses. FIGS. 16A and 16B are SI reconstructed high resolution UV-AutoM images of mouse brain samples with a thickness of 100 μm and 200 μm, respectively, while FIGS. 16C and 16D are corresponding virtually-stained H&E images. Successful color mapping from UV-AutoM contrast to H&E-stained version greatly facilitates UV-AutoM imaging modality to be developed as a practical intraoperative diagnosis tool that can be used by medical doctors and pathologists in an operating room.

Figure 17C:
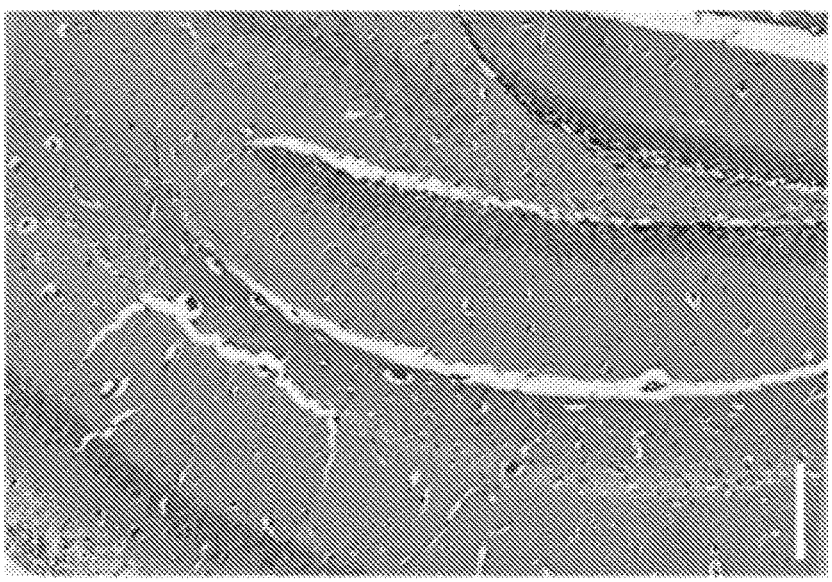
FIG. 17C shows an example of bright-field H&E-stained image corresponding to the mouse brain sample imaged in FIGS. 17A and 17B.
Figure 17B:
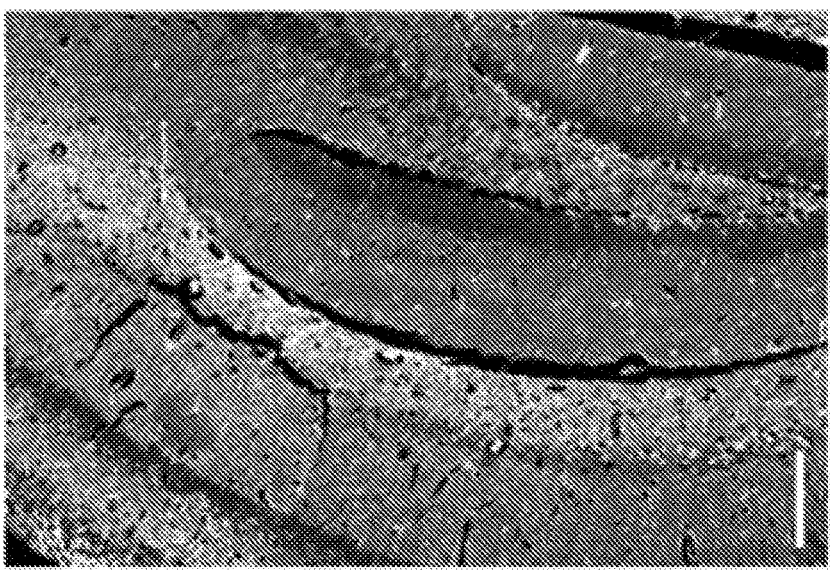
FIG. 17B shows an example of a UV-AutoM image of the hippocampus region imaged in FIG. 17A.
Figure 17A:
FIG. 17A shows an example of label-free UV-PAM image of a hippocampus region from a deparaffinized FFPE mouse brain sample with 7-µm thickness, wherein the UV-PAM image was generated using the system of FIG. 3.

It will be appreciated that a complementary contrast exits between UV-PAM and UV-AutoM images which thereby enables a method and system of generating both UV-PAM and UV-AutoM images. Photon (or fluorescence) is generated via radiative relaxation while heat is generated via non-radiative relaxation, in which PA wave is released via the heat-induced pressure/temperature rise of the sample. Consequently, PA and autofluorescence images are expected to exhibit a complementary contrast in accordance with the conservation of energy. This contrast is experimetnally demonstrated in FIGS. 17A and 17B. With UV laser (266 nm) excitation, FIG. 17A shows the label-free PA contrast (UV-PAM), whereas FIG. 17B shows the label-free autofluorescence contrast (UV-AutoM), of a hippocampus region from a deparaffinized FFPE mouse brain sample with 7-μm thickness. FIG. 17C is the corresponding bright-field H&E-stained image, which shows structural similarity with both UV-PAM and UV-AutoM images. Since the strong absorption of nucleus in the UV range, the nuclei concentrated at hippocampus appear bright in UV-PAM image while dark in UV-AutoM image. Such complementary imaging contrast mechanism enable a dual-modality label-free imaging facility to provide more structural and functional information of unprocessed fresh tissue.

Throughout this description, brain samples were extracted from Swiss Webster mice and subsequently fixed in 10% neutral-buffer formalin at room temperature for 24 hours. For thin slices (2-8 μm), the samples were processed by FFPE workflow and sectioned by a microtome. The FFPE tissue sections were deparaffinized using xylene and mounted on quartz slides to be imaged by the described UV-PAM and UV-AutoM systems, and followed by H&E staining procedures. For thick slices (20 200 μm), the samples were directly cut by a vibratome with different target thickness.

Although the invention has been described with reference to a preferred embodiment, it will be appreciated by those skilled in the art that the invention may be embodied in other forms.

The advantageous embodiments and/or further developments of the above disclosure—except for example in cases of clear dependencies or inconsistent alternatives—can be applied individually or also in arbitrary combinations with one another.

The invention claimed is:

1. A computer-implemented method of generating a pseudo-hematoxylin and eosin (H&E) stained image, wherein the method includes:

receiving an input image, the input image being an ultraviolet-based autofluorescence microscopy (UV-AutoM) image or an ultraviolet-based photoacoustic microscopy (UV-PAM) image of an unlabeled specimen, wherein the input image is a grayscale image;

transforming the input image, using a generative adversarial network, to a pseudo-H&E stained image of the input image; and outputting the pseudo-H&E stained image;

wherein the input image received in the form of a UV-AutoM image is an estimated UV-AutoM image generated from a sequence of speckle illuminated images captured according to a scanning trajectory, each speckle illuminated image of the sequence being an image obtained by illuminating the unlabeled specimen with a UV light beam formed with a speckle pattern, wherein the estimated UV-AutoM image has a higher resolution compared to each speckle illuminated image of the sequence, and wherein the estimated UV-AutoM image is generated by:
   a) initializing a high resolution image object based on interpolating an average of the sequence of speckle illuminated images;
   b) for each speckle illuminated image of the sequence:
      i) generating the estimated speckle illuminated image by computationally shifting the high resolution image object to a specific position in the scanning trajectory;
      ii) determining a filtered object-pattern compound in the frequency domain based on the estimated speckle illuminated image in the frequency domain and optical transfer function;
      iii) determining an updated estimated speckle illuminated image in the frequency domain based on the estimated speckle illuminated image in the frequency domain, the respective captured speckle illuminated image in the frequency domain, the filtered object pattern compound in the frequency domain, and the optical transfer function;
      iv) updating the high resolution object based on the updated estimated speckle illuminated image, the estimated speckle illuminated image in the spatial domain, and the speckle pattern;
      v) updating the speckle pattern based on the updated estimated speckle illuminated image, the estimated speckle illuminated image, and the high resolution image object; and
      vi) applying Nesterov momentum acceleration to the high resolution image object and the speckle pattern; and
   c) iteratively performing step b) until convergence of reconstructing the high resolution image object is detected, the high resolution image object being the estimated UV-AutoM image with enhanced subcellular resolution across centimeter-scale imaging area.

2. The computer-implemented method of claim 1, wherein the generative adversarial network is a generative adversarial network with cycle consistency.

3. The computer-implemented method of claim 1, wherein the generative adversarial network comprises of four deep convolutional neural networks including:
   a first generator deep convolutional neural network configured to transform the input image to a generated H&E image;
   a second generator deep convolutional neural network configured to transform a H&E image to a generated UV-AutoM or UV-PAM image;
   a first discriminator deep convolutional neural network configured to discriminate between a H&E image of a training set and a generated H&E image generated by the first generator deep convolutional neural network; and
   a second discriminator deep convolutional neural network configured to discriminate between a UV-AutoM or UV-PAM image of the training set and a generated UV-AutoM or UV-PAM image generated by the second generator deep convolutional neural network.

4. The computer-implemented method according to claim 1, wherein the input image received in the form of the UV-PAM image is generated by:
   controlling a galvo-mirror scanner of a focusing assembly to focus ultraviolet light on a specimen according to a scanning trajectory;
   receiving, by at least one transducer, photoacoustic waves emitted by the specimen in response to the ultraviolet light; and
   generating, based on the photoacoustic waves, the UV-PAM image.

5. The computer-implemented method according to claim 3, wherein the first and second generator deep convolutional neural networks are ResNet-based or U-Net-based generator networks.

6. The computer-implemented method according to claim 3, wherein the first and second discriminator deep convolutional neural networks are PatchGAN discriminator networks.

7. A computer system configured to generate a pseudo-hematoxylin and eosin (H&E) stained image, wherein the computer system includes one or more memories having stored therein executable instructions, and one or more processors, wherein execution of the executable instructions by the one or more processors cause the one or more processors to:
   receive an input image, the input image being an ultraviolet-based autofluorescence microscopy (UV-AutoM) image or an ultraviolet-based photoacoustic microscopy (UV-PAM) image of an unlabeled specimen, wherein the input image is a grayscale image;
   transform the input image, using a generative adversarial network, to a pseudo-H&E stained image of the input image; and
   output the pseudo-H&E stained image;
   wherein the input image received in the form of a UV-AutoM image is an estimated UV-AutoM image generated from a sequence of speckle illuminated images captured according to a scanning trajectory, each speckle illuminated image of the sequence being an image obtained by illuminating the unlabeled specimen with a UV light beam formed with a speckle pattern, wherein the estimated UV-AutoM image has a higher resolution compared to each speckle illuminated image of the sequence, and wherein the estimated UV-AutoM image is generated by the one or more processors by:
   a) initializing a high resolution image object based on interpolating an average of the sequence of speckle illuminated images;
   b) for each speckle illuminated image of the sequence:
      i) generating the estimated speckle illuminated image by computationally shifting the high resolution image to a specific position in the scanning trajectory;
      ii) determining a filtered object-pattern compound in the frequency domain based on the estimated speckle illuminated image in the frequency domain, and an optical transfer function;
      iii) determining an updated estimated speckle illuminated image in the frequency domain based on the estimated speckle illuminated image in the frequency domain, the respective captured speckle illuminated image in the frequency domain, the filtered object pattern compound in the frequency domain, and the optical transfer function;
      iv) updating the high resolution object based on the updated estimated speckle illuminated image, the estimated speckle illuminated image in the spatial domain, and the speckle pattern;
      v) updating the speckle pattern based on the updated estimated speckle illuminated image, the estimated speckle illuminated image, and the high resolution image object; and vi) applying Nesterov momentum acceleration to the high resolution image object and the speckle pattern; and c) iteratively performing step b) until convergence of reconstructing the high resolution image object is detected, the high resolution image object being the estimated UV-AutoM image with enhanced subcellular resolution across centimeter-scale imaging area.

8. The computer system of claim 7, wherein the generative adversarial network is a generative adversarial network with cycle consistency.

9. The computer system of claim 7, wherein the generative adversarial network comprises of four deep convolutional neural networks including:
   a first generator deep convolutional neural network configured to transform the input image to a generated H&E image;
   a second generator deep convolutional neural network configured to transform a H&E image to a generated UV-AutoM or UV-PAM image;
   a first discriminator deep convolutional neural network configured to discriminate between a H&E image of a training set and a generated H&E image generated by the first generator deep convolutional neural network; and
   a second discriminator deep convolutional neural network configured to discriminate between a UV-AutoM or UV-PAM image of the training set and a generated UV-AutoM or UV-PAM image generated by the second generator deep convolutional neural network.

10. The computer system according to claim 7, wherein the input image received in the form of the UV-PAM image is generated by:
   controlling a galvo-mirror scanner of a focusing assembly to focus ultraviolet light on a specimen according to a scanning trajectory;
   receiving, by at least one transducer, photoacoustic waves emitted by the specimen in response to the ultraviolet light; and
   generating, based on the photoacoustic waves, the UV-PAM image.

11. The computer system according to claim 9, wherein the first and second generator deep convolutional neural networks are ResNet-based or U-Net-based generator networks.

12. The computer system according to claim 9, wherein the first and second discriminator deep convolutional neural networks are PatchGAN discriminator networks.

13. One or more non-transitory computer readable mediums including executable instructions which configure a computer system to generate a pseudo-hematoxylin and eosin (H&E) stained image, wherein the computer system has one or more processors, wherein execution of the executable instructions by the one or more processors configures the computer system to:
   receive an input image, the input image being an ultraviolet-based autofluorescence microscopy (UV-AutoM) image or an ultraviolet-based photoacoustic microscopy (UV-PAM) image of an unlabeled specimen, wherein the input image is a grayscale image;
   transform the input image, using a generative adversarial network, to a pseudo-H&E stained image of the input image; and
   output the pseudo-H&E stained image;
   wherein the input image received in the form of a UV-AutoM image is an estimated UV-AutoM image generated from a sequence of speckle illuminated images captured according to a scanning trajectory, each speckle illuminated image of the sequence being an image obtained by illuminating the unlabeled specimen with a UV light beam formed with a speckle pattern, wherein the estimated UV-AutoM image has a higher resolution compared to each speckle illuminated image of the sequence, and wherein the estimated UV-AutoM image is generated by:
   a) initializing a high resolution image object based on interpolating an average of the sequence of speckle illuminated images;
   b) for each speckle illuminated image of the sequence:
      i) generating the estimated speckle illuminated image by computationally shifting the high resolution image object to a specific position in the scanning trajectory;
      ii) determining a filtered object-pattern compound in the frequency domain based on the estimated speckle illuminated image in the frequency domain and optical transfer function;
      iii) determining an updated estimated speckle illuminated image in the frequency domain based on the estimated speckle illuminated image in the frequency domain, the respective captured speckle illuminated image in the frequency domain, the filtered object pattern compound in the frequency domain, and the optical transfer function;
      iv) updating the high resolution object based on the updated estimated speckle illuminated image, the estimated speckle illuminated image in the spatial domain, and the speckle pattern;
      v) updating the speckle pattern based on the updated estimated speckle illuminated image, the estimated speckle illuminated image, and the high resolution image object; and
      vi) applying Nesterov momentum acceleration to the high resolution image object and the speckle pattern; and
   c) iteratively performing step b) until convergence of reconstructing the high resolution image object is detected, the high resolution image object being the estimated UV-AutoM image with enhanced subcellular resolution across centimeter-scale imaging area.

14. The one or more non-transitory computer readable mediums of claim 13, wherein the generative adversarial network is a generative adversarial network with cycle consistency.

* * * * *